US011505572B2

(12) United States Patent
Fautsch et al.

(10) Patent No.: US 11,505,572 B2
(45) Date of Patent: *Nov. 22, 2022

(54) THERAPEUTICS FOR THE TREATMENT OF GLAUCOMA

(71) Applicants: Mayo Foundation for Medical Education and Research, Rochester, MN (US); Regents of the University of Minnesota, Minneapolis, MN (US)

(72) Inventors: Michael P. Fautsch, Rochester, MN (US); Peter Dosa, Vadnais Heights, MN (US); Michael A. Walters, Minneapolis, MN (US); Gunda I. Georg, St. Paul, MN (US)

(73) Assignees: Mayo Foundation for Medical Education and Research, Rochester, MN (US); Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/077,859

(22) Filed: Oct. 22, 2020

(65) Prior Publication Data

US 2021/0040148 A1 Feb. 11, 2021

Related U.S. Application Data

(63) Continuation of application No. 15/113,773, filed as application No. PCT/US2015/013955 on Jan. 30, 2015, now Pat. No. 10,981,951.

(60) Provisional application No. 61/934,310, filed on Jan. 31, 2014.

(51) Int. Cl.
| | |
|---|---|
| *A61K 31/353* | (2006.01) |
| *C07K 5/062* | (2006.01) |
| *C07D 405/04* | (2006.01) |
| *C07D 405/12* | (2006.01) |
| *C07D 285/24* | (2006.01) |
| *A61K 31/549* | (2006.01) |
| *A61K 31/454* | (2006.01) |
| *A61K 31/4025* | (2006.01) |
| *A61K 9/00* | (2006.01) |
| *A61K 31/675* | (2006.01) |
| *A61K 31/4439* | (2006.01) |
| *C07D 201/00* | (2006.01) |
| *C07D 311/20* | (2006.01) |
| *C07D 311/70* | (2006.01) |
| *C07D 405/14* | (2006.01) |
| *C07F 9/6547* | (2006.01) |
| *C07F 9/6558* | (2006.01) |

(52) U.S. Cl.
CPC .......... *C07K 5/06026* (2013.01); *A61K 9/00* (2013.01); *A61K 9/0048* (2013.01); *A61K 9/0051* (2013.01); *A61K 31/353* (2013.01); *A61K 31/4025* (2013.01); *A61K 31/4439* (2013.01); *A61K 31/454* (2013.01); *A61K 31/549* (2013.01); *A61K 31/675* (2013.01); *C07D 201/00* (2013.01); *C07D 285/24* (2013.01); *C07D 311/20* (2013.01); *C07D 311/70* (2013.01); *C07D 405/04* (2013.01); *C07D 405/12* (2013.01); *C07D 405/14* (2013.01); *C07F 9/6547* (2013.01); *C07F 9/65586* (2013.01)

(58) Field of Classification Search
CPC .................................................... A61K 31/353
See application file for complete search history.

(56) References Cited

U.S. PATENT DOCUMENTS

| | | | |
|---|---|---|---|
| 2,986,573 A | 5/1961 | Topliss et al. |
| 3,251,837 A | 5/1966 | Holland et al. |
| 3,361,816 A | 1/1968 | Topliss et al. |
| 4,200,640 A | 4/1980 | Nagano et al. |
| 4,409,222 A | 10/1983 | Arrigoni-Martelli |
| 4,616,012 A | 10/1986 | Neustadt et al. |
| 4,634,698 A | 1/1987 | Andrews et al. |
| 5,013,853 A | 5/1991 | Gericke et al. |
| 5,328,830 A | 7/1994 | Janis et al. |
| 5,565,560 A | 10/1996 | Goulet et al. |
| 5,965,620 A | 10/1999 | Sorgente et al. |
| 5,985,856 A | 11/1999 | Valentino et al. |

(Continued)

FOREIGN PATENT DOCUMENTS

| | | |
|---|---|---|
| EP | 120428 A1 | 10/1984 |
| EP | 366273 A1 | 5/1990 |

(Continued)

OTHER PUBLICATIONS 2017-0002040 A1, U.S. Appl. No. 15/113,773, Fautsch et al., Jan. 5, 2017.

(Continued)

*Primary Examiner* — John S Kenyon
(74) *Attorney, Agent, or Firm* — Knowles Intellectual Property Strategies, LLC

(57) ABSTRACT

The present invention provides benzothiadiazine and chroman derivatives and particularly diazoxide and cromakalim derivatives for use in treating glaucoma, retinopathy, treating age related macular degeneration, treating, stabilizing and/or inhibiting blood and lymph vascularization, and reducing intraocular pressure by administering a pharmaceutically effective amount of a prodrug disposed in an ophthalmically acceptable carrier to the eye, wherein the prodrug specifically modulates a $K_{ATP}$ channel to reduce an intraocular pressure.

37 Claims, 8 Drawing Sheets

(56) References Cited

U.S. PATENT DOCUMENTS

| | | | |
|---|---|---|---|
| 6,242,443 | B1 | 6/2001 | Nordisk |
| 6,572,848 | B1 | 6/2003 | Breton et al. |
| 6,872,838 | B2 | 3/2005 | Stella et al. |
| 7,186,707 | B2 | 3/2007 | Prokai et al. |
| 8,063,054 | B2 | 11/2011 | Lazdunski et al. |
| 10,981,951 | B2 * | 4/2021 | Fautsch .............. A61K 31/4025 |
| 2006/0025386 | A1 | 2/2006 | Lazdunski et al. |
| 2009/0149451 | A1 | 6/2009 | Cowen |
| 2010/0113379 | A1 | 5/2010 | Rubinsztein et al. |
| 2013/0150329 | A1 | 6/2013 | Singh et al. |
| 2014/0221326 | A1 | 8/2014 | Demopulos et al. |
| 2017/0002040 | A1 | 1/2017 | Fautsch et al. |
| 2017/0165241 | A1 | 6/2017 | Markowitz et al. |
| 2018/0134761 | A1 | 5/2018 | Lindhout et al. |
| 2018/0243281 | A1 | 8/2018 | Andres et al. |
| 2019/0224217 | A1 | 7/2019 | Hazan et al. |

FOREIGN PATENT DOCUMENTS

| | | |
|---|---|---|
| JP | 2011/136923 | 7/2011 |
| WO | WO 1989/05808 | 6/1989 |
| WO | WO 1989/10757 | 11/1989 |
| WO | WO 1991/08741 | 6/1991 |
| WO | WO 2013/130411 A1 | 9/2013 |
| WO | WO 2015/117024 A1 | 8/2015 |

OTHER PUBLICATIONS

Attwood et al., "Synthesis of Homochiral Potassium Channel Openers: Role of the Benzopyranyl 3-Hydroxyl Group in Cromakalim and Pyridine N-Oxides in Determining the Biological Activities of Enantiomers" Bioorg. Med. Chem. Lett. 1992, 2, 229.

Ashwood et al.,"Synthesis and antihypertensive activity of 4-(cyclic amido)-2h-1-benphyrans," J. Med. Chem. 29:2194-2201, Jan. 1, 1986.

Brayden, J.E. et al., "Role of Potassium Channels in the Vascular Response to Endogeneous and Pharmacological Vasodilators" Blood Vessels, 1991, 28, 147.

Buckle et al., "Structural Modifications of the Potassium Channel Activator Cromakalim: The C-3 Position" J. Chem. Soc. Perkin Trans. 1991, 1, 63-70.

Cecchetti et al., Current Topics in Medicinal Chemistry, 2016, 6, 1049.

Chiang et al, "Effect of cromakalim and nicorandil on intraocular pressure after topical administration in rabbit eyes," J. Ocular Pharmacol Therapeut., 11(3): 195-201, Jan. 1, 1995.

Chowdhury et al., "Analogs of the ATP-Sensitive Potassium (KATP) Channel Opener Cromakalim with in Vivo Ocular Hypotensive Activity," J. Med. Chem., 59(13):6221-6231, 2016.

Chowdhury et al., "ATP-Sensitive Potassium (KATP) Channel Openers Diazoxide and Nicorandil Lower Intraocular Pressure in Vivo," IOVS., 54(7):4892-4899, Jul. 2013.

Chowdhury et al., "ATP sensitive potassium channel openers: A new class of ocular hypotensive agents," Experimental Eye Research, 158:85-93, 2017.

Chowdhury et al., "ATP-Sensitive Potassium (KATP) Channel Activation Decreases Intraocular Pressure in the Anterior Chamber of the Eye," IOVS., 52(9):6435-6442, Aug. 2011.

Chowdhury et al., "ATP-sensitive potassium (KATP) channel openers diazoxide and nicorandil lower intraocular pressure by activating the Erk 1/2 signaling pathway," PLOS One., Jun. 8, 2017, 18 pages.

Chowdhury et al., "Effect of Cromakalim Prodrug 1 (CKLP1) on Aqueous Humor Dynamics and Feasibility of Combination Therapy With Existing Ocular Hypotensive Agents," IOVS., 58:5731-5742, 2017.

Chowdhury et al., "Ocular Hypotensive Effects of the ATPSensitive Potassium Channel Opener Cromakalim in Human and Murine Experimental Model Systems," Plos One., 10(11):e0141783, Nov. 4, 2015, 16 pages.

European Search Report in International Application No. 15743644.5, dated Jul. 14, 2017, 15 pages.

Extended European Search Report in International Application No. 15743644.5, dated Dec. 7, 2017, 18 pages.

Ettaiche, et al., "ATP-sensitive potassium channels K(ATP)) in retina: a key role for delayed ischemic tolerance" Brain Research 2001, 890, 118-129.

European Search Report in International Application No. 15743644.5, dated Jun. 21, 2019, 25 pages.

Howe, C.L. et al., Neuroprotection mediated by inhibition of calpain during acute viral encephalitis Scientific Reports 2016, 6, 28699.

International Preliminary Report on Patentability in International Application No. PCT/US2015/013955, dated Aug. 11, 2016, 15 pages.

International Search Report and Written Opinion in International Application No. PCT/US2015/13955, dated Jun. 26, 2015, 11 pages.

Invitation to Pay Additional Fees in International Application No. PCT/US2015/13955, dated Apr. 23, 2015.

Quast, U. et al., "In vitro and in vivo comparison of two K + channel openers, diazoxide and cromkalim, and their inhibition by glibenclamide" Journal of Pharmacology and Experimental Therapeutics 1989, 250, 261.

Rautio et al., "Prodrugs: design and clinincal application," Nat. Rev. Drug Discov., 7(3):255-270, Mar. 2008, 16 pages.

Sebille et al., "Recent Developments in the Chemistry of Potassium Channel Activators: The Cromakalim Analogs" Current Medicinal Chemistry 2014, 11, 1213.

Barot, M. et al., "Prodrugs Strategies in Ocular Drug Delivery." Accessed Jul. 6, 2018. Medicinal Chemistry (2012), vol. 8, pp. 753-768. (Year: 2012).

Patel, A., et al. "Ocular drug delivery systems: An overview." Accessed Jul. 6, 2018. World J. Pharmacol. (2013), vol. 2, Issue 2, pp. 47-64. Available from: <https://www.ncbi.nhm.nih.gov/pmc/articles/PMC4289909/pdf/nihms641436.pdf> (Year: 2013).

Kumari, A., et al., "Ocular inserts—Advancement in therapy of eye diseases." J. Adv. Pharm. Technol. Res. Accessed Jul. 6, 2018. (printable> (Year: 2010).

Glaucome Center of Excellence. Johns Hopkins University. "Can glaucoma be cured?" © Nov. 8, 2012. Accessed Jul. 6, 2018. Available from: <https://www.hopkinsmedicine.org/wilmer/services/glaucome/book/chapter_can_glaucoma_be_cured.html> (Year: 2012).

Mainolfi, N., et al. "An Effective Profrug Strategy to Selectively Enhance Ocular Exposure of a Cannabinoid Receptor (CB1/2) Agonist." Accessed Jul. 6, 2018. J. Med. Chem. (2013), vol. 56, pp. 5464-5472. (Year: 2013).

Chowdhury, U.R., et al. "ATP-Sensitive Potassium (KATP) Channel Openers Diazoxide and Nicorandil Lower Intraocular Pressure in Vivo." Investigative Ophthalmology and Visual Science. Accessed Jul. 6, 2018 (Jul. 2013), vol. 54, No. 7, pp. 4892-4899, (Year: 2013).

Enzo Life Sciences. "Diazoxide." © Aug. 19, 2009. Accessed Jul. 9, 2018. Available from: <http://www.enzolifesciences.com/ALX-550-260/diazoxide/> (Year: 2009).

Ghelardini, C., et al. "Influence of potassium channel modulators on cognitive processes in mice." Accessed Jul. 9, 2018. (1998) British Journal of Pharmacology. vol. 123, pp. 1079-1084. (Year: 1998).

Chowdhury, Uttio R. et. al. "Effect of ATP-sensitive Potassium Channel Openers on Intraocular Pressure in Ocular Hypertensive Animal Models," Glaucoma, IOVS, vol. 63, No. 2, Article 15:3, Feb. 7, 2022, 11 pages.

Chowdhury, Uttio Roy et al. "Pharmacological Profile and Ocular Hypotensive Effects of Cromakalim Prodrug 1, a Novel ATP-Sensitive Potassium Channel Opener, in Normotensive Dogs and Nonhuman Primates," Journal of Ocular Pharmacology and Therapeutics, vol. 37, No. 5, 2021, pp. 251-260.

Chowdhury, Uttio Roy et al. "Pharmacology and safety profile of the ATP-sensitive potassium channel opening prodrug CKLP1 in preclinical large animal models," Ocular hypertension abstract—TM Society—Dec. 10, 2021.

Fautsch, Michael et al. "Effect of ATP-Sensitive Potassium ($K_{atp}$) Channel Openers on Intraocular Pressure (IOP) and Aqueous Humor Dynamics in Preclinical Ocular Hypertensive Models," Ocular hypertension, ISER, Oct. 2021, 1 page.

(56) References Cited

OTHER PUBLICATIONS

Fautsch, Michael et al. "Effect of ATP-sensitive potassium channel openers on intraocular pressure in ocular hypertensive animal models," Pharmacology abstract—TM Society—Dec. 11, 2021.

Steel, Cynthia L. "Preclinical Efficacy and Safety Profile of QLS-101, a Novel ATP-Sensitive Potassium Channel Opener for the Reduction of IOP," AOPT Talk, Qlaris Bio, Inc., Feb. 24, 2021, 14 pages.

Steel, Cynthia L. et al. "Ocular hypotensive properties and biochemical profile of QLS-101, a novel ATP-sensitive potassium ($K_{ATP}$) channel opening prodrug," Qlaris Bio, Inc., Association for Ocular Pharmacology and Therapeutics (AOPT)—presentation Feb. 24, 2021, 26 pages.

Steel, Cynthia L. et al. "Preclinical Efficacy and Safety Profile of a Novel Episcleral Venous Pressure (EVP)-Lowering Agent," American Glaucoma Society—Poster Feb. 15, 2021, 1 page.

Steel, Cynthia L. et al. "Ocular Tissue Conversion and Activity Profile of QLS-101, a Novel Topical IOP-Lowering Therapeutic," Association for Research in Vision and Ophthalmology (ARVO), Qlaris Bio, Inc. Poster, Apr. 15, 2021, 1 page.

Torrejon, Karen Y., et al. "Use of a Novel Potassium Channel Opener in a 3D-Glaucomatous Human Trabecular Meshwork/Schlemm's Canal Tissue Model," Association for Research in Vision and Ophthalmology, Glauconix Poster—Preclinical data Apr. 15, 2021, 1 page.

Wirostko, Barbara M., et al. "Systemic and Ocular Toxicology and Pharmacokinetic Profiles of QLS-101, a Novel topical IOP-Lowering Therapeutic," Association for Research in Vision and Ophthalmology Qlaris Poster—In vivo preclinical data Apr. 14, 2021, 1 page.

* cited by examiner

THERAPEUTICS FOR THE TREATMENT OF GLAUCOMA

PRIORITY

This application is a continuation of U.S. patent application Ser. No. 15/113,773, filed Jul. 22, 2016, which is a National Stage Application under 35 U.S.C. § 371 of International Application No. PCT/US2015/013955, filed Jan. 30, 2015, which claims the benefit of U.S. Provisional Application No. 61/934,310, filed Jan. 31, 2014. Each of these references is incorporated in their entirety.

STATEMENT OF FEDERALLY FUNDED RESEARCH

This invention was made with government support under EY021727 and TR000114 awarded by the National Institutes of Health. The government has certain rights in the invention.

TECHNICAL FIELD OF THE INVENTION

The present invention relates generally to benzothiadiazine and chroman derivatives and particularly diazoxide and cromakalim derivatives and methods for treating glaucoma and reducing intraocular pressure. It also relates to a process for their preparation and pharmaceutical compositions in which they are present.

BACKGROUND ART

Without limiting the scope of the invention, its background is described in connection with methods and compositions for treating glaucoma and reducing intraocular pressure. Glaucoma is a group of conditions, which causes a characteristic and progressive optic neuropathy and is the leading cause of irreversible blindness in the world. It is estimated that there are 67 million people in the world with glaucoma; 6.7 million of whom are blind from the condition. There is no cure for glaucoma, a condition which leads to a reduction in visual field and ultimately, legal blindness. Since intraocular pressure is the only modifiable risk factor/causative agent for glaucoma, treatments focus on reducing the intraocular pressure in the eye to slow glaucoma progression and blindness. Glaucoma is classified according to three parameters, the underlying cause which is classified as primary (idiopathic) or secondary (associated with some other ocular or systemic conditions); the state of the anterior chamber angle, classified as open angle (open access of the outflowing aqueous humor to trabecular meshwork) or closed angle (narrow angle where the trabecular meshwork is blocked by apposition of the peripheral iris and the cornea); and chronicity, which may be acute or chronic. The most common form of glaucoma is primary open angle glaucoma.

Treatments for glaucoma range from laser trabeculoplasty to topical treatment. For example, selective laser trabeculoplasty is a laser treatment of the trabecular meshwork as a means to improve the outflow of aqueous humor from the eye, thereby reducing intraocular pressure. Topical treatments are used to slow aqueous humor production or increase aqueous humor drainage. Both processes will help to decrease intraocular pressure. However, glaucoma medical adherence with topical medication is poor, and studies suggest that fewer than half of the patients are able to maintain consistently lowered intraocular pressure with topical agents. In addition, current intraocular pressure lowering drugs such as brimonidine, timolol, and prostaglandin analogs can have significant side effects.

U.S. Pat. No. 8,063,054, entitled, "Method of Treatment of Retinal Ischemia with Diazoxide" discloses a composition including diazoxide (7-chloro-3-methyl-2H-1,2,4-benzothiadiazine-1,1-dioxide) for the treatment and/or prevention of retinal ischemia and of diseases associated with retinal ischemia. Ischemia is a restriction in blood supply to tissues, causing a shortage of oxygen and glucose needed for cellular metabolism (to keep tissue alive). Ischemia is generally caused by problems with blood vessels, with resultant damage to or dysfunction of tissue. In addition, the compositions are soluble in organic solvents.

U.S. Pat. No. 7,186,707, entitled, "Prodrugs for use as Ophthalmic Agents," discloses a mechanism by which steroidal quinol compounds confer beneficial ophthalmic effects. The subject compounds possess a lipophilic-hydrophilic balance for transcorneal penetration and are readily reduced into parent phenolic A-ring steroid compounds to provide protection or treatment against various ocular symptoms and disorders. These prodrugs confer lipid solubility optimal for transcorneal penetration and are readily converted to endogenous reducing agents into active phenolic A-ring steroid compounds.

U.S. Pat. No. 5,985,856, entitled, "Prodrugs and Methods of Making and Using the Same," discloses prodrugs of parent drugs and methods of making and using the same. The prodrugs comprise an amine-containing parent drug moiety and a prodrug moiety, such as methoxyphosphonic acid or ethoxyphosphonic acid. The prodrugs may be employed in therapy for the treatment of various indications, such as pain, and in methods of decreasing the abuse potential of abuse-prone drugs and/or delaying the onset of parent drug activity and/or prolonging parent drug activity as compared to administration of a parent drug.

U.S. Pat. No. 5,965,620, entitled, "Methods and Compositions for ATP-sensitive K+ Channel Inhibition for Lowering Intraocular Pressure," discloses ATP-sensitive K+ channel modulating compounds are incorporated into ophthalmically acceptable carriers for administration to the eye in order to affect intraocular pressure.

DISCLOSURE OF THE INVENTION

The present invention provides benzothiadiazine and chroman derivatives and particularly diazoxide and cromakalim derivatives for use in treating glaucoma, ocular hypertension, retinopathy, treating age related macular degeneration, treating, stabilizing and/or inhibiting blood and lymph vascularization, and reducing intraocular pressure.

The present invention provides a method for reducing intraocular pressure in an eye of a patient by administering a pharmaceutically effective amount of a prodrug disposed in an ophthalmically acceptable aqueous carrier to the eye, wherein the prodrug or released drug specifically modulates a $K_{ATP}$ channel, wherein the prodrug has the formula:

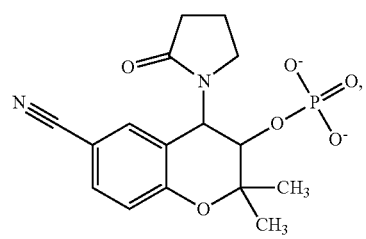

-continued

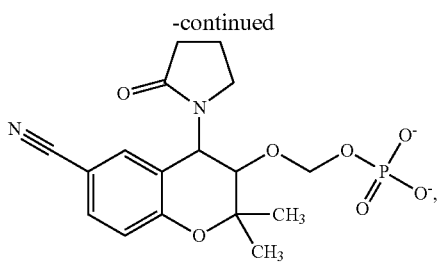

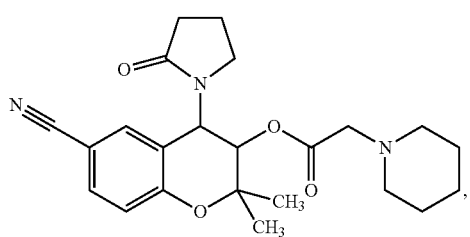

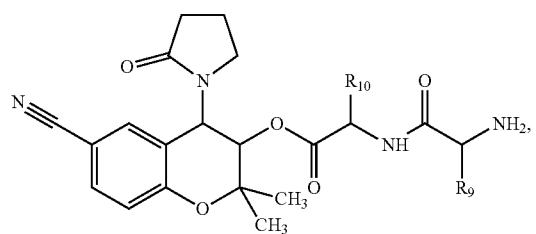

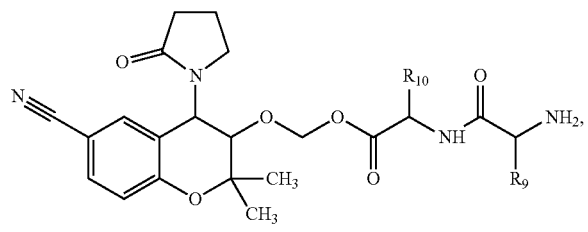

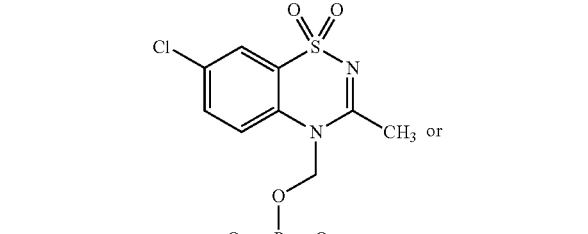

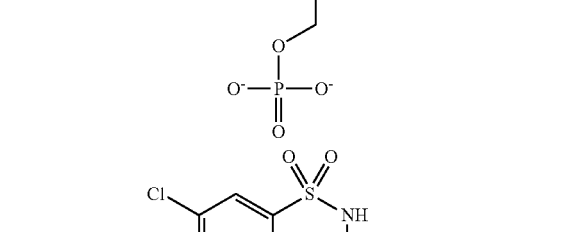

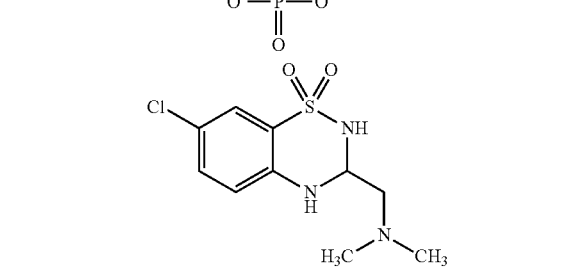

wherein R9 and R10 may independently be a —H; —CH₂CHCH₃CH₃; —CHCH₃CH₃; —CH₃; —CHCH₃CH₂CH₃; —CH₂(CH₂)₃NH₂; —CH₂CH₂SCH₃; —CH₂OH; or —CHOHCH₃.

The present invention provides a pharmaceutical composition comprising: a benzothiadiazine or chroman derivative disposed in an ophthalmically acceptable aqueous carrier. The benzothiadiazine derivative has the formula:

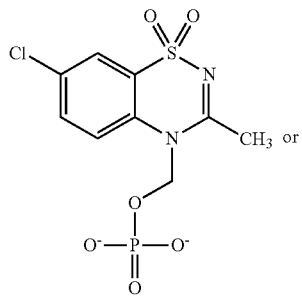

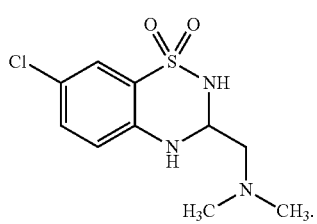

The chroman derivative has the formula:

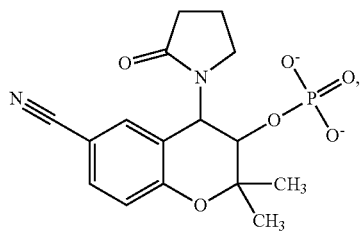

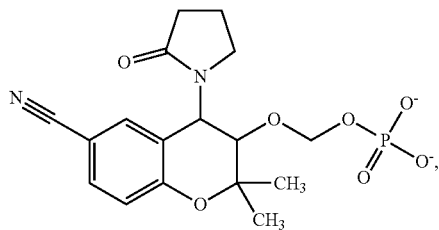

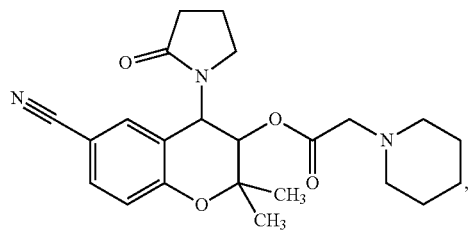

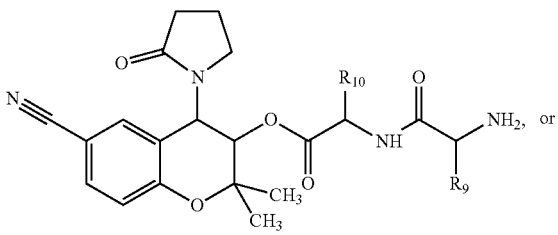

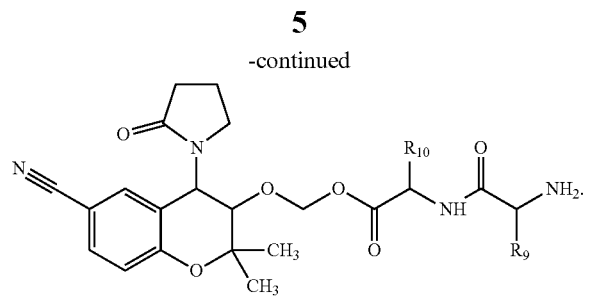

The present invention provides a method for treating ocular hypertension and glaucoma in an eye of a patient by identifying a patient suffering from glaucoma in an eye; administering a pharmaceutically effective amount of a prodrug disposed in an ophthalmically acceptable carrier to the eye, wherein the prodrug specifically modulates a $K_{ATP}$ channel to reduce intraocular pressure and treat glaucoma, wherein the prodrug has the formula:

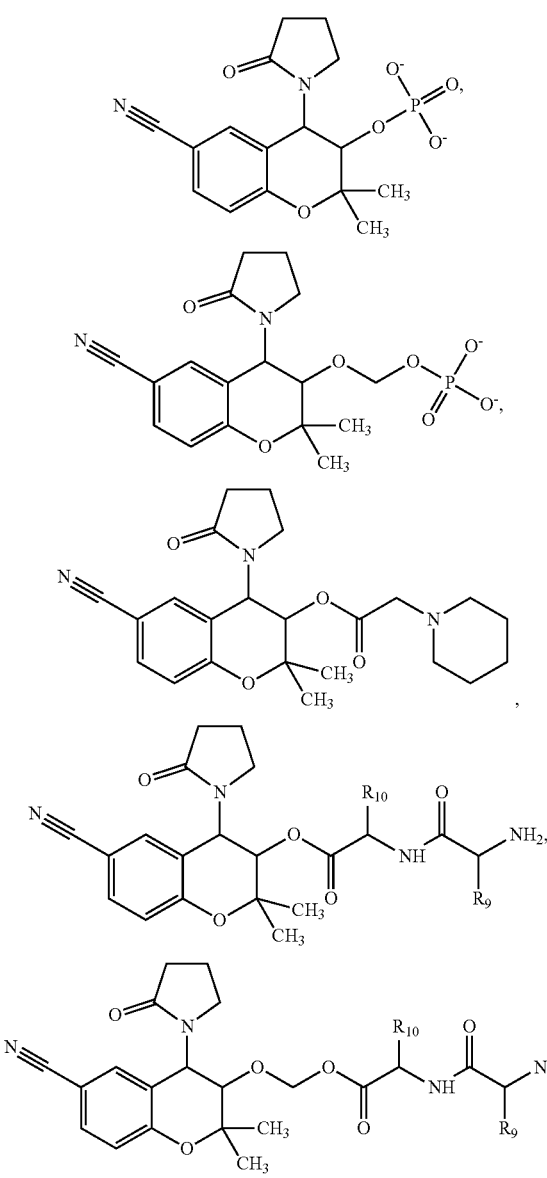

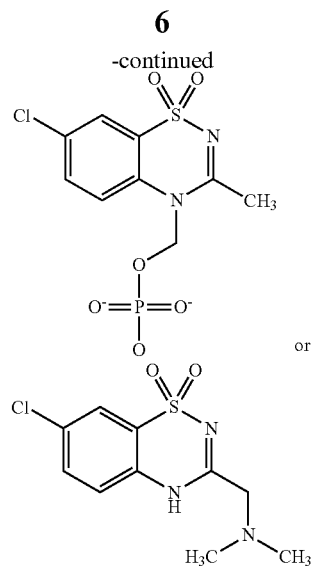

wherein R9 and R10 may independently be a —H; —CH$_2$CHCH$_3$CH$_3$; —CHCH$_3$CH$_3$; CH$_3$; —CHCH$_3$CH$_2$CH$_3$; —CH$_2$(CH$_2$)$_3$NH$_2$; —CH$_2$CH$_2$SCH$_3$; —CH$_2$OH; or —CHOHCH$_3$.

The present invention provides a cromakalim derivative compound having the formula:

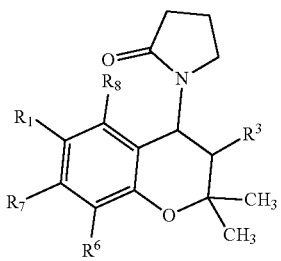

wherein R3 is a prodrug moiety of the formula:

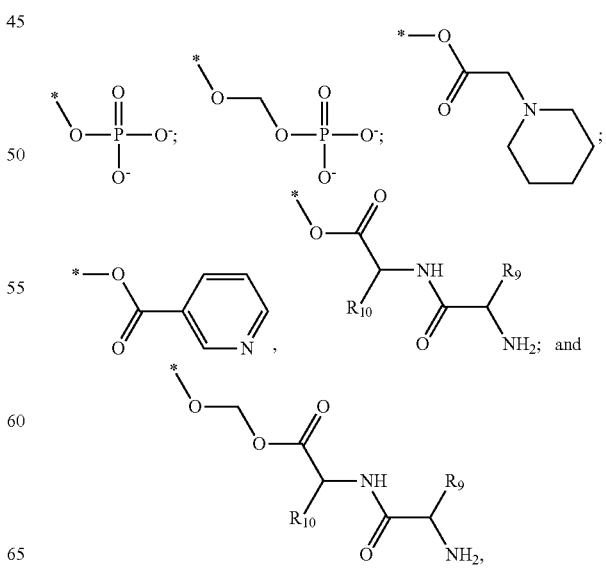

wherein R9 and R10 may independently be a —H; —CH$_2$CHCH$_3$CH$_3$; —CHCH$_3$CH$_3$; —CH$_3$; —CHCH$_3$CH$_2$CH$_3$; —CH$_2$(CH$_2$)$_3$NH$_2$; —CH$_2$CH$_2$SCH$_3$; —CH$_2$OH; or —CHOHCH$_3$.

The present invention provides a diazoxide derivative compound having the formula:

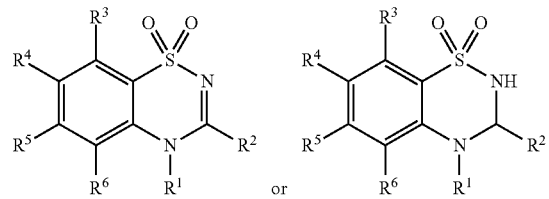

wherein R1 or R2 is a prodrug moiety of the formula:

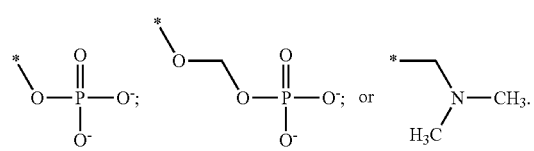

The present invention provides a method for treating glaucoma in an eye of a patient by identifying a patient suffering from glaucoma or an elevated TOP in an eye; administering a pharmaceutically effective amount of a prodrug disposed in an ophthalmically acceptable carrier to the eye, wherein the prodrug specifically modulates a K$_{ATP}$ channel to reduce intraocular pressure and treat glaucoma, wherein the prodrug has the formula:

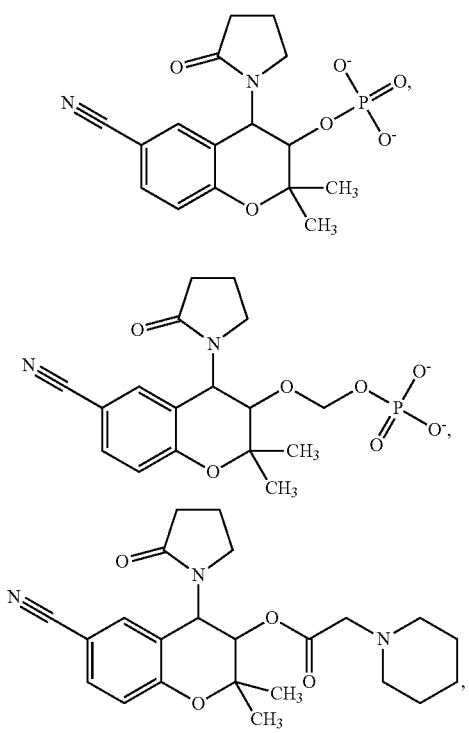

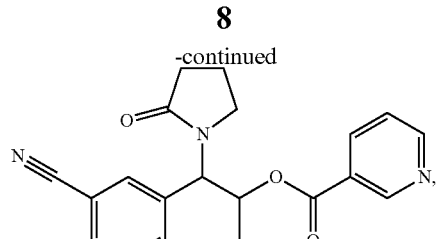

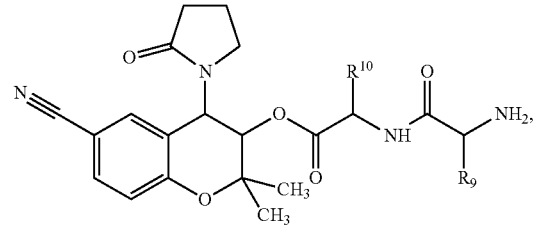

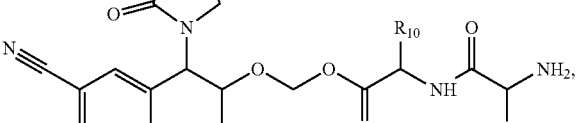

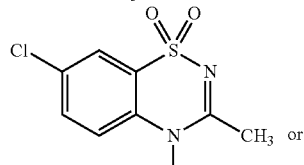

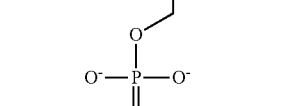

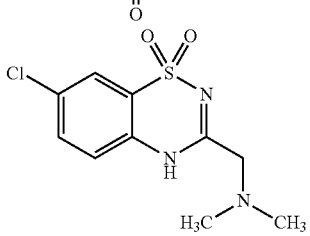

wherein R9 and R10 may independently be a —H; —CH$_2$CHCH$_3$CH$_3$; —CHCH$_3$CH$_3$; CH$_3$; —CHCH$_3$CH$_2$CH$_3$; —CH$_2$(CH$_2$)$_3$NH$_2$; —CH$_2$CH$_2$SCH$_3$; —CH$_2$OH; or —CHOHCH$_3$. The dosages are administered from 1 to 4 times per day.

DESCRIPTION OF THE DRAWINGS

For a more complete understanding of the features and advantages of the present invention, reference is now made to the detailed description of the invention along with the accompanying figures and in which.

DESCRIPTION OF EMBODIMENTS

Figures 1A, 1B:
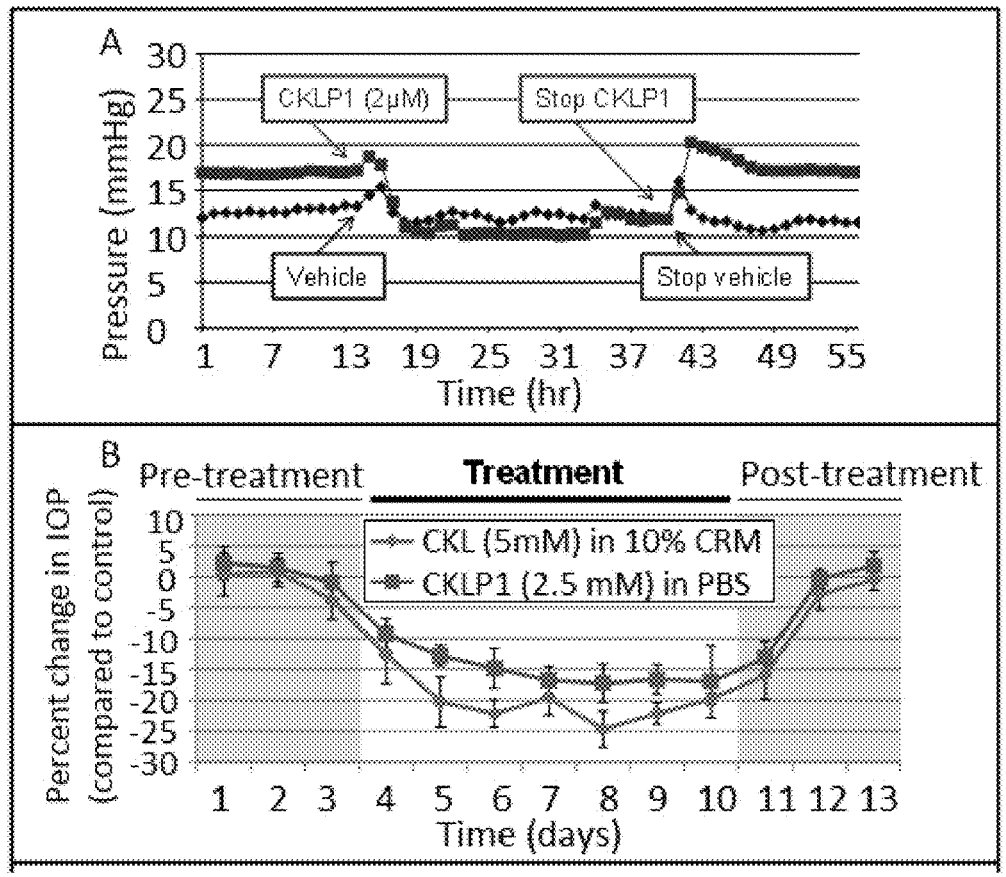
FIG. 1A is a graph of a pair of anterior eye segments showing the addition of CKLP1 (2 μM) that results in the reduction of pressure.
FIG. 1B is a graph of the change in C57BL/6 mice intraocular pressure following treatment with cromakalim in DMSO or CKLP1 in aqueous carrier.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, an "effective dosage" or "effective amount" of a prodrug, drug, compound, or pharmaceutical composition is an amount that is expected to be or is sufficient to effect beneficial or desired results. For therapeutic use, beneficial or desired results include results such as suppressing or reducing the onset and/or development of a disease or condition or decreasing one or more symptoms resulting from a disease or condition that is responsive to parent drug therapy, including increasing the quality of life of those suffering from a disease or condition responsive to parent drug therapy and/or decreasing the dose of the same or other medications, drugs, compounds or pharmaceutical compositions required to treat the disease or condition and/or decreasing or eliminating one or more side effects associated with a medication required to treat the individual's disease or condition. As used herein, "effective dosage" refers to the dosage of a prodrug, drug, compound, or pharmaceutical composition an amount sufficient to accomplish prophylactic or therapeutic treatment either directly or indirectly. An effective dosage can be administered in one or more administrations. As is understood in the clinical context, an effective dosage of a prodrug, drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "pharmaceutically acceptable carrier" includes any material which, when combined with an active ingredient, allows the ingredient to retain biological activity. Examples include, but are not limited to, any of the standard pharmaceutical carriers and any suitable ophthalmically acceptable carrier such as a phosphate buffered saline solution, water, emulsions such as oil/water emulsion, and various types of wetting agents. Compositions comprising such carriers may be formulated by conventional methods.

As used herein, "parent composition" refers to a composition that does not contain a prodrug moiety.

As used herein, "prodrug moiety" or "PM," refers to any group attached to a composition that is not present in the parent composition.

As used herein, "prodrug" refers to a derivative of a biologically active compound that may independently have pharmaceutical activity or may lack pharmaceutical activity but is converted to an active agent. A prodrug, according to the present invention, may be converted into an active compound through one or more steps.

As used herein, "pharmaceutically acceptable prodrugs," refers to those prodrugs of the compounds which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention.

As used herein, "Alkyl" refers to linear, branched or cyclic hydrocarbon structures preferably having from 1 to 20 carbon atoms (a "$C_1$-$C_{20}$ alkyl") e.g., 1 to 10 carbon atoms or 1 to 6 carbon atoms. This term is exemplified by groups such as methyl, t-butyl, n-heptyl, octyl, cyclobutylmethyl, cyclopropylmethyl and the like. "Unsubstituted alkyl" refers to an alkyl group that is not substituted with any additional substituents. When an alkyl residue having a specific number of carbons is named, all geometric isomers having that number of carbons are intended to be encompassed; thus, for example, "butyl" is meant to include n-butyl, sec-butyl, isobutyl and t-butyl.

As used herein, "Substituted alkyl" refers to an alkyl group of from 1 to 10 carbon atoms, having from 1 to 5 substituents, including but not limited to, groups such as halogen, alkoxy, acyl, acylamino, acyloxy, amino, hydroxyl, mercapto, carboxyl, aryl, cyano, nitro and the like. For instance, an alkaryl group (alkyl-aryl) is a substituted alkyl and includes moieties such as propylbenzene where the moiety is attached to the parent structure via the aryl or the alkyl portion, most preferably via the alkyl portion of the substituent.

As used herein, "Alkenyl" refers to linear, branched or cyclic hydrocarbon structures preferably having from 2 to 20 carbon atoms (a "$C_1$-$C_{20}$ alkenyl") and more preferably 2 to 10 carbon atoms or 2 to 6 carbon atoms and having at least 1 site of alkenyl unsaturation.

As used herein, "Unsubstituted alkenyl" refers to an alkenyl group that is not substituted with any additional substituents. When an alkenyl residue having a specific number of carbons is named, all geometric isomers having that number of carbons are intended to be encompassed. This term is exemplified by groups such as propen-3-yl (—CH$_2$—CH=CH$_2$), 3-methyl-but-2-enyl and (=CH$_2$). The group represented by =CH$_2$ indicates connectivity from, e.g., an sp2 hybridized carbon atom of a parent structure to CH$_2$ via a double bond.

As used herein, "Substituted alkenyl" refers to an alkenyl group, preferably a C$_2$-C$_{10}$ alkenyl, having from 1 to 5 substituents, including but not limited to, substituents such as halogen, alkoxy, acyl, acylamino, acyloxy, amino, hydroxyl, mercapto, carboxyl, aryl, cyano, nitro and the like.

As used herein, "Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

As used herein, "Substituted alkoxy" refers to the group "substituted alkyl-O—".

As used herein, "Alkoxyalkyl" refers to the group "alkyl-O-alkyl-" which includes, by way of example, methoxy methyl and the like.

As used herein, "Alkanoate" refers to "alkyl-C(=O)—O—" which includes, by way of example, ethanoate and pentanoate. "Alkyl-Alkanoate" refers to "-alkyl-O—C(=O) alkyl" such as in —CH(CH$_2$CH$_3$)—O—C(=O)—CH$_3$.

As used herein, "Carbonylalkyl" refers to —C(=O)-alkyl, which includes, by way of example, —C(=O)—CH$_2$CH$_3$.

As used herein, "Alkoxyphosphonic acid" refers to "alkyl —O—P(=O)(OH)$_2$" or when referred to or implied as a moiety attached to a parent structure, the radical "-alkyl-O—P(=O)(OH)$_2$" such that the alkoxyphosphonic acid is attached to a parent structure via the alkyl moiety. This term is exemplified by groups such as methoxyphosphonic acid and ethoxyphosphonic acid and their radicals —CH$_2$—O—P(=O)(OH)$_2$—CH(CH$_3$)OP(O)(OH)$_2$ and —CH$_2$CH$_2$—O—P(=O)(OH)$_2$.

As used herein, "Alkylcarbonylalkoxy" refers to alkyl-C (=O)—O-alkyl. In one variation, the alkylcarbonylalkoxy refers to a moiety C$_1$-C$_4$ alkyl-C(=O)—O—C$_1$-C$_6$ alkyl. An exemplary alkylcarbonylalkoxy is —CH$_2$CH$_2$C(=O) OCH$_3$.

As used herein, "C$_3$-C$_8$ monocyclic cycloalkyl" as used herein is a 3-, 4-, 5-, 6-, 7- or 8-membered saturated non-aromatic monocyclic cycloalkyl ring. Representative C$_3$-C$_8$ monocyclic cycloalkyl groups include, but are not limited to, cyclopropyl, cyclobutyl, cyclopentyl, cyclohexyl, cycloheptyl and cyclooctyl. In one embodiment, the C$_3$-C$_8$ monocyclic cycloalkyl group is substituted with one or more of the following groups: -halo, —O—(C$_1$-C$_6$ alkyl), —OH, —CN, —COOR', —OC(O)R', —N(R)$_2$, —NHC(O)R' or —C(O)NHR' groups wherein each R' is independently —H or unsubstituted —C$_1$-C$_6$ alkyl. Unless indicated, the C$_3$-C$_8$ monocyclic cycloalkyl is unsubstituted.

As used herein, "C$_3$-C$_8$ monocyclic cycloalkenyl" as used herein is a 3-, 4-, 5-, 6-, 7- or 8-membered non-aromatic monocyclic carbocyclic ring having at least one endocyclic double bond, but which is not aromatic. It is to be understood that when any two groups, together with the carbon atom to which they are attached form a C$_3$-C$_8$ monocyclic cycloalkenyl group, the carbon atom to which the two groups are attached remains tetravalent. Representative C$_3$-C$_8$ monocyclic cycloalkenyl groups include, but are not limited to, cyclopropenyl, cyclobutenyl, 1,3-cyclobutadienyl, cyclopentenyl, 1,3-cyclopentadienyl, cyclohexenyl, 1,3-cyclohexadienyl, cycloheptenyl, 1,3-cycloheptadienyl, 1,4-cycloheptadienyl, 1,3,5-cycloheptatrienyl, cyclooctenyl, 1,3-cyclooctadienyl, 1,4-cyclooctadienyl, or 1,3,5-cyclooctatrienyl. In one embodiment, the C$_3$-C$_8$ monocyclic cycloalkenyl group is substituted with one or more of the following groups: -halo, —O—(C$_1$-C$_6$ alkyl), —OH, —CN, —COOR', —OC(O)R', —N(R')$_2$, —NHC(O)R' or —C(O) NHR' groups wherein each R' is independently —H or unsubstituted —C$_1$-C$_6$ alkyl. Unless indicated, the C$_3$-C$_9$ monocyclic cycloalkenyl is unsubstituted.

The term "halo" as used herein refers to —F, —Cl, —Br or —I.

The term "3- to 7-membered monocyclic heterocycle" refers to: a 3-, 4-, 5-, 6-, or 7-membered aromatic or non-aromatic monocyclic cycloalkyl in which 1-4 of the ring carbon atoms have been independently replaced with an NH, an O, or an S moiety. The non-aromatic 3- to 7-membered monocyclic heterocycles can be attached via a ring nitrogen, sulfur, or carbon atom. The aromatic 3- to 7-membered monocyclic heterocycles are attached via a ring carbon atom. Representative examples of a 3- to 7-membered monocyclic heterocycle group include, but are not limited to furanyl, furazanyl, imidazolidinyl, imidazolinyl, imidazolyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, triazolyl, In one embodiment, the 3- to 7-membered monocyclic heterocycle group is substituted with one or more of the following groups: -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl. Unless indicated, the 3- to 7-membered monocyclic heterocycle is unsubstituted.

The term "direct administration," as used herein refers to the compounds being applied topically, or by injection or instillation, into the eye. Such direct administration does not include systemic forms of administration, such as oral or parenteral administration, e.g., intramuscular, subcutaneous, or intraperitoneal injection although the present invention may also be administered by this method. Direct administration of the modulating compounds of the present invention is intended to introduce the compounds directly into the eye so that they will be transported into the anterior chamber where the compounds will be effective to lower intraocular pressure, by enhancing the transport or release of intraocular fluid from the anterior chamber or by decreasing fluid production.

The present invention shows both CKLP-1 and its enantiomer are active in vivo in eyes. The enantiomer of CKLP1 is referred to as "ent-CKLP1". CKLP1 can be synthesized from levcromakalim while ent-CKLP1 can be synthesized from (+)-cromakalim.

The methods and compositions of the present invention are also intended to reduce intraocular pressure conditions of the eye to a point where optic nerve damage is slowed. Such conditions may result from a variety of causes, such as surgery for glaucoma, retinal detachment, uveitis, and the like. The methods and compositions of the present invention rely on administering compounds which specifically modulate, i.e. inhibit or potentiate the K$_{ATP}$ channel compounds directly to the eye of the patient or host. In some instances, the compositions may be administered to reduce the intraocular pressures to below 20 mmHg, or preferably between 10-20 mmHg, more preferably between 10-15 mmHg, or between 12-15 mmHg.

The $K_{ATP}$ channel is regulated by intracellular adenosine triphosphate (ATP) such that it is spontaneously active in the absence of ATP and closed by increasing ATP concentration in the cytoplasmic side of the membrane. The $K_{ATP}$ channel is not activated by intraocular $Ca^{+2}$, and gating of the channel is independent of membrane potential. $K_{ATP}$ channels are regulated by changes in the intracellular concentration of ATP and have been found in cells from various tissues such as cardiac cells, pancreatic cells, skeletal muscles, smooth muscles, central neurons and adenohypophysis cells. $K_{ATP}$ channels are found in a variety of different human tissues and have different effects clinically depending on that tissue. The $K_{ATP}$ channels have been associated with diverse cellular functions for example hormone secretion (insulin from pancreatic beta-cells, growth hormone and prolactin from adenohypophysis cells), vasodilation (in smooth muscle cells), cardiac action potential duration, neurotransmitter release in the central nervous system.

$K_{ATP}$ channels are octamers made up of 4 copies of a K+ inward rectifying ($K_{ir}$) subunit ($K_{ir}$ 6.1 or $K_{ir}$ 6.2) and 4 parts of a sulfonylurea receptor (SUR) subunit (SUR1, SUR2A, or SUR2B). At least 6 different $K_{ATP}$ channels can be made of the different $K_{ir}$ and SUR subunits and thus the $K_{ATP}$ channel openers represent a heterogeneous group of compounds. Currently, the known $K_{ATP}$ channel openers have poor aqueous solubility and are not used in therapeutic application for treating glaucoma and intraocular pressure. $K_{ATP}$ channel openers have been found to relax vascular smooth muscles and have therefore been used for the treatment of hypertension. In addition, $K_{ATP}$ channel openers can be used as bronchodilators in the treatment of asthma and various other diseases. Furthermore, $K_{ATP}$ channel openers have been shown to promote hair growth, and have been used for the treatment of baldness. $K_{ATP}$ channel openers are also able to relax urinary bladder smooth muscle and therefore, can be used for the treatment of urinary incontinence. $K_{ATP}$ channel openers which relax smooth muscle of the uterus can be used for treatment of premature labor. $K_{ATP}$ channel openers which act on the central nervous system can be used for treatment of various neurological and psychiatric diseases such as Alzheimer, epilepsy and cerebral ischemia. However, $K_{ATP}$ channel openers in the prior art have poor aqueous solubility and are generally unsuited for use in ocular tissues. As a result, the skilled artisan would generally not study or look to $K_{ATP}$ channels modulators for use in ocular tissues. This is supported by the lack of studies of $K_{ATP}$ channels modulators in ocular tissues. For example, U.S. Pat. No. 6,242,443, entitled "1,2,4-benzothiadiazine derivatives, their preparation and use'" discloses 1,2,4-benzothiadiazine derivative compounds useful in the treatment of diseases of the central nervous system, the cardiovascular system, the pulmonary system, the gastrointestinal system and the endocrinological system. However, these compositions were dissolved in DMSO, added to a buffer and added to pancreatic β-cell for testing. In another study Diazoxide was dissolved in a pure solution of dimethyl sulfoxide (DMSO) and diluted in sterile physiological serum to obtain a final ophthalmic solution at 0.01% active principle and 0.4% DMSO. Thus the prior art $K_{ATP}$ channels modulators are not aqueous soluble and not suitable for use in ocular tissues.

The present invention provides aqueous soluble $K_{ATP}$ channel modulators that function in ocular tissues to reduce intraocular pressure which is both surprising and unexpected as $K_{ATP}$ channel openers in the prior art have poor aqueous solubility and are generally unsuited for use in ocular tissues. In addition the aqueous soluble benzothiadiazine and chroman derivative $K_{ATP}$ channel modulators of the present invention are effective at concentrations at equal to or lower than the parent composition. For example the benzothiadiazine and chroman derivatives maybe administered at concentrations up to 75% less than the parent composition concentration, e.g., 75, 70, 65, 60, 55, 50, 45, 40, 35, 30, 25, 20, 15, 10, 5 or incremental variations thereof of the concentration of the parent composition.

Compounds useful in the present invention will specifically modulate the $K_{ATP}$ channels in the eye. Thus, a decrease in intraocular pressure occurs when the eye is treated with $K_{ATP}$ channel openers and no change in intraocular pressure occurs when the eye is treated with $K_{ATP}$ channel closer.

Some embodiments of the present invention includes diazoxide and cromakalim prodrugs, diazoxide and cromakalim derivative, and substituted diazoxide and cromakalim compositions that are aqueous soluble and function as $K_{ATP}$ channel openers to reduce intraocular pressure. These compositions provide surprising and unexpected results as $K_{ATP}$ channel modulators that function in ocular tissues to reduce intraocular pressure.

The present invention includes benzothiadiazine and chroman derivatives that may be prodrugs and/or derivative compositions, and more particularly to diazoxide and cromakalim prodrugs and derivatives, for treating glaucoma and elevated intraocular pressure. It also relates to a process for their preparation and pharmaceutical compositions in which they are present.

The composition also includes prodrugs and/or derivative compositions that show activity in the prodrugs and/or derivative form without removal of the prodrug moiety. As such, the prodrug may be administered without need to be converted to an active form to treat glaucoma and/or elevated intraocular pressure. In addition, compositions of the present invention are aqueous soluble.

In one embodiment, the present invention includes benzothiadiazine and chroman derivatives and more particularly to diazoxide and cromakalim prodrugs and derivative that are aqueous soluble and can be used to treat glaucoma and elevated intraocular pressure.

In one embodiment, the present invention includes diazoxide and cromakalim prodrugs, diazoxide and cromakalim derivative, and substituted diazoxide and cromakalim compositions that are aqueous soluble and can be used to treat glaucoma and elevated intraocular pressure.

In one embodiment, the present invention provides a series of prodrugs of cromakalim, using both racemic and optically active cromakalim (levcromakalim) as starting materials.

Levcromakalim may also be called (3S,4R)-3-hydroxy-2,2-dimethyl-4-(2-oxopyrrolidin-1-yl)chroman-6-carbonitrile or (3S,4R)-3,4-dihydro-3-hydroxy-2,2-dimethyl-4-(2-oxo-1-pyrrolidinyl)2H-1-benzopyran-6-carbonitrile.

Levcromakalim (the optically active cromakalim) is generally referred to as being in the (3S, 4R)-configuration. The ent-CKLP1 would thus be (3R, 4S). All compounds tested so far showed biological activity in a normotensive mouse. For example, CKLP1 showed good activity in both the mouse and rabbit models and in an ex vivo human eyeball model.

Two phosphate prodrugs were made and tested in racemic forms: rac-CKLP1 and rac-CKLP2. CKLP1 has since been synthesized in an optically active form starting from levcromakalim.

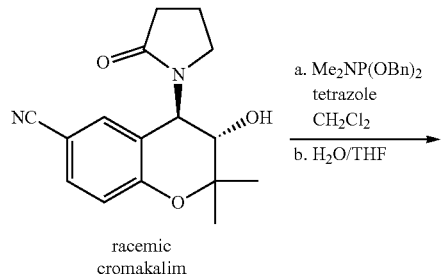

racemic cromakalim a. Me$_2$NP(OBn)$_2$
   tetrazole
   CH$_2$Cl$_2$
b. H$_2$O/THF

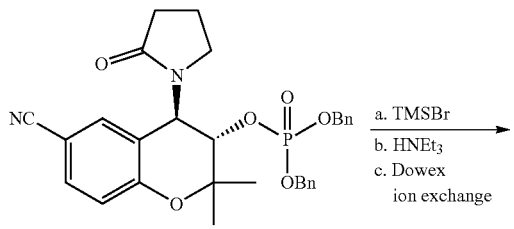

a. TMSBr
b. HNEt$_3$
c. Dowex ion exchange

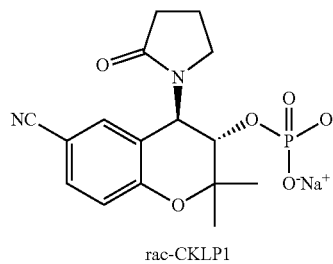

rac-CKLP1

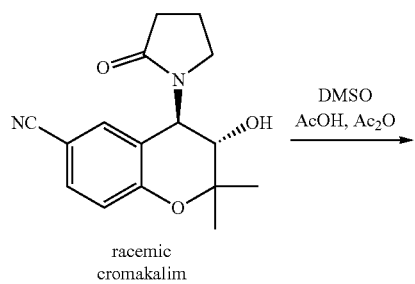

racemic cromakalim

DMSO
AcOH, Ac$_2$O

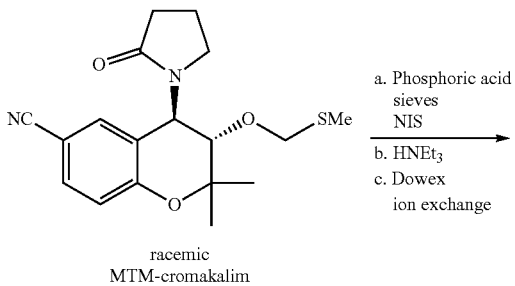

racemic MTM-cromakalim a. Phosphoric acid
   sieves
   NIS
b. HNEt$_3$
c. Dowex ion exchange

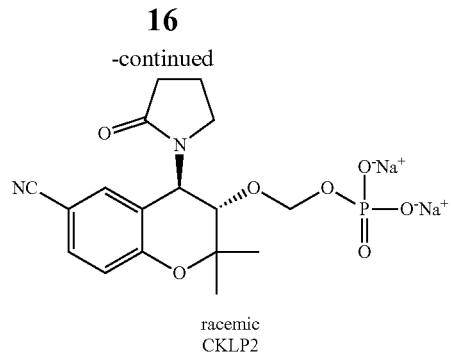

racemic CKLP2

Optically active CKLP1 has been synthesized via the same route starting from levcromakalim instead of racemic cromakalim.

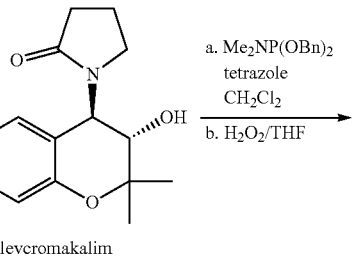

levcromakalim a. Me$_2$NP(OBn)$_2$
   tetrazole
   CH$_2$Cl$_2$
b. H$_2$O$_2$/THF

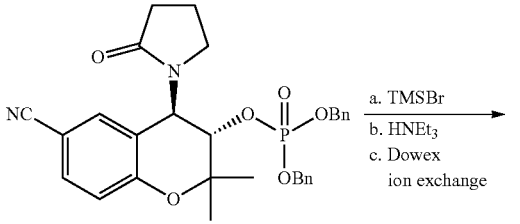

a. TMSBr
b. HNEt$_3$
c. Dowex ion exchange

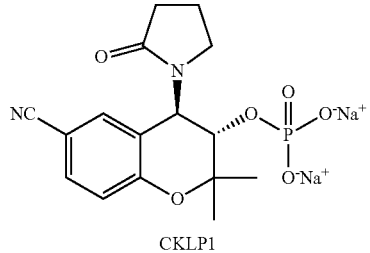

CKLP1

The enantiomer of CKLP1, referred to as ent-CKLP1, has been synthesized from the same route starting from (+)-cromakalim.

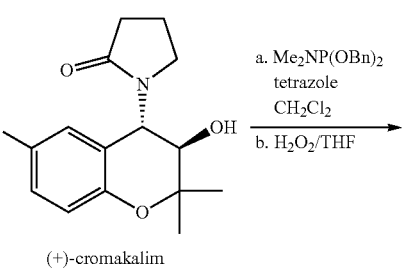

(+)-cromakalim a. Me$_2$NP(OBn)$_2$
   tetrazole
   CH$_2$Cl$_2$
b. H$_2$O$_2$/THF -continued

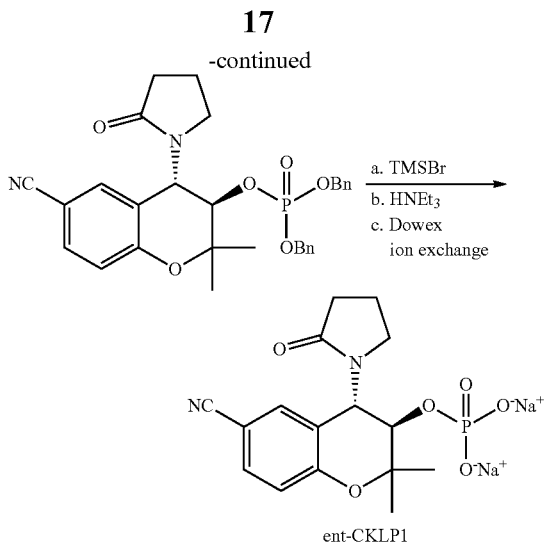

ent-CKLP1

FIG. 1A is a graph of pressure readings obtained from a pair of human anterior eye segments where one eye was treated with a $K_{ATP}$ channel opener prodrug (CKLP1) while the fellow anterior segment was treated with vehicle alone. Results show that addition of CKLP1 (2 µM) reduces pressure in human anterior segment perfusion organ culture. FIG. 1B is a graph of pressure change obtained in normotensive C57BL/6 mice following treatment with parent (CKL) and prodrug (CKLP1).

Figure 2:
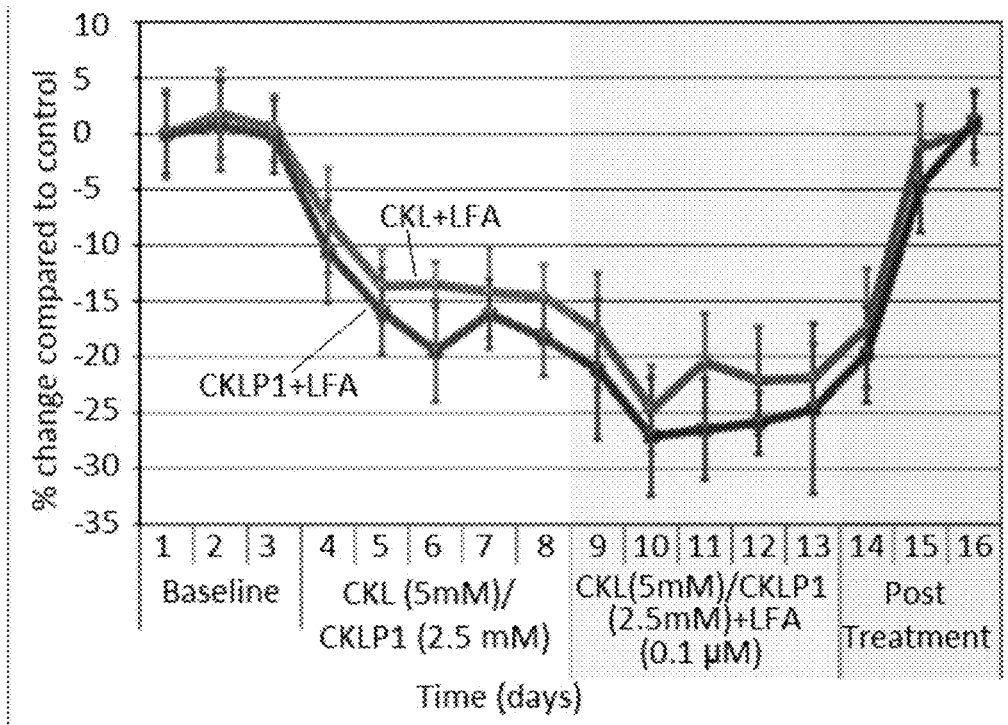
FIG. 2 is a graph of the combination treatment in mice with CKL/CKLP1 and prostaglandin showing additive effects. CKL: −12.77±2.38, CKL+LFA: −21.43±1.85 CKLP1: −16.11±2.61, CKLP1+LFA: −26.06±2.98.

FIG. 2 is a graph of the combination treatment in mice with CKL/CKLP1 and prostaglandin analog latanoprost free acid (LFA) that shows additive effects: −12.77±2.38, CKL+LFA: −21.43±1.85 CKLP1: −16.11±2.61, CKLP1+LFA: −26.06±2.98.

Figure 3:
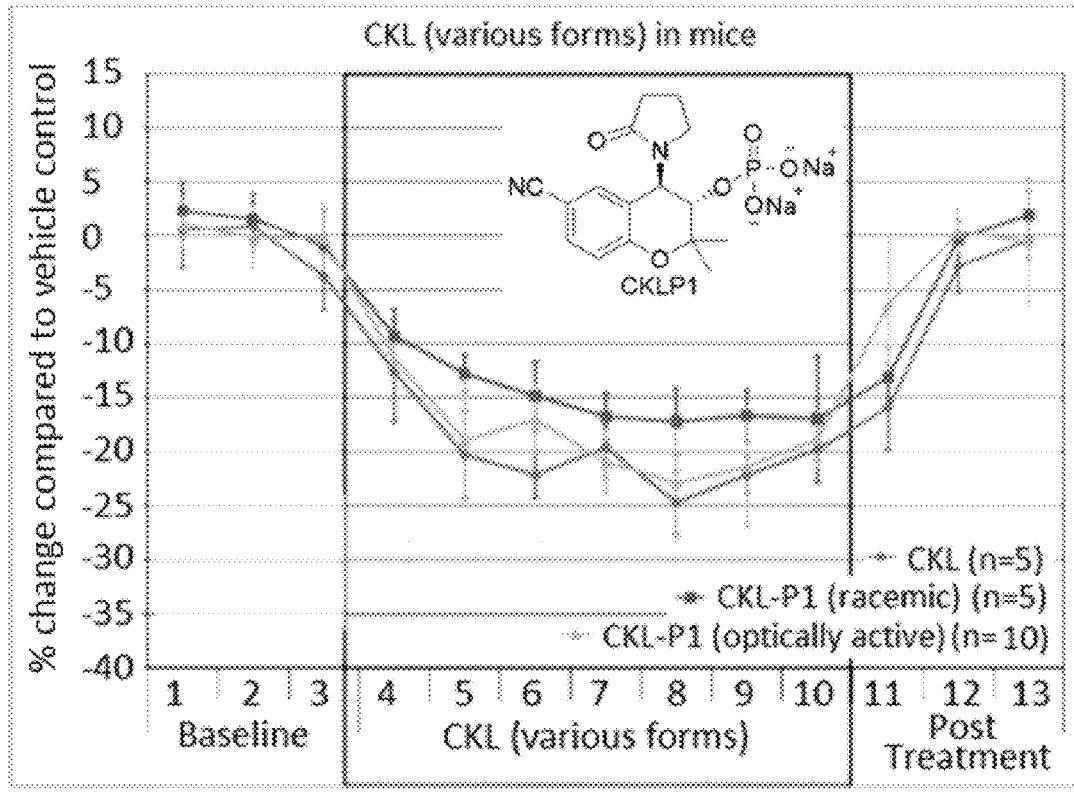
FIG. 3 is a graph showing the treatment with various forms of CKL.
Figure 4:
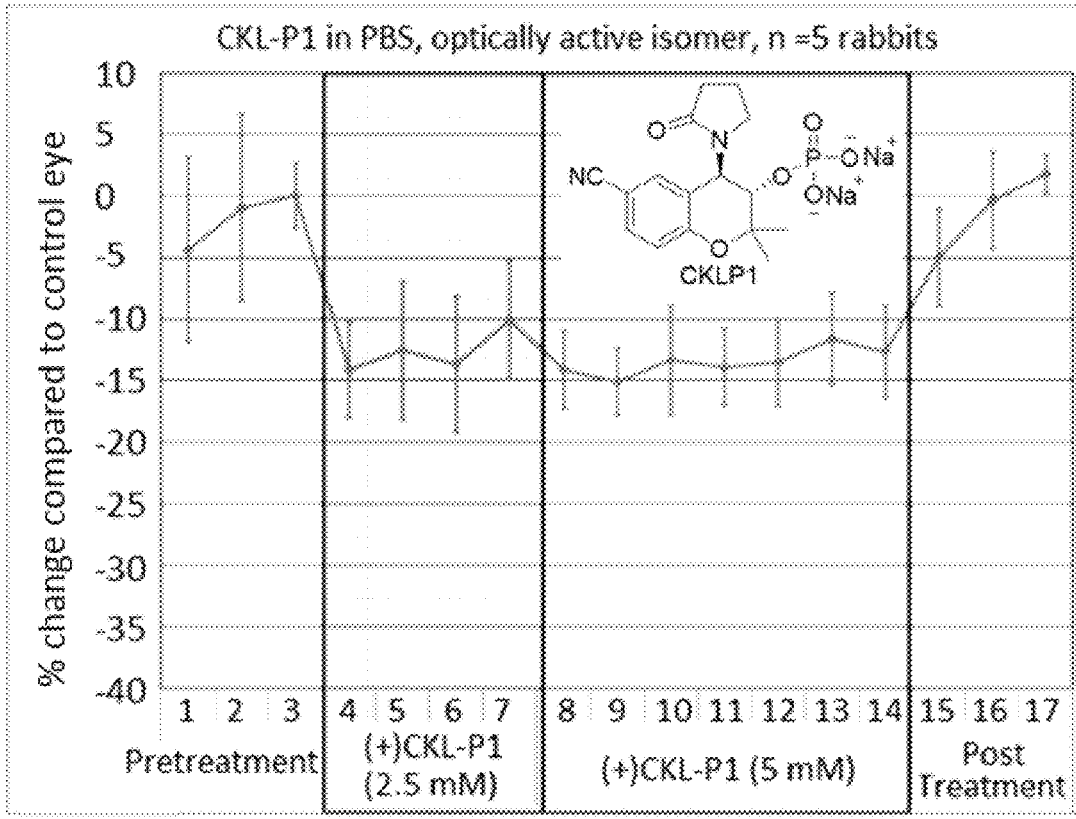
FIG. 4 is a graph showing the treatment of rabbits with CKL-P1 in PBS, optically active isomer.
Figure 5:
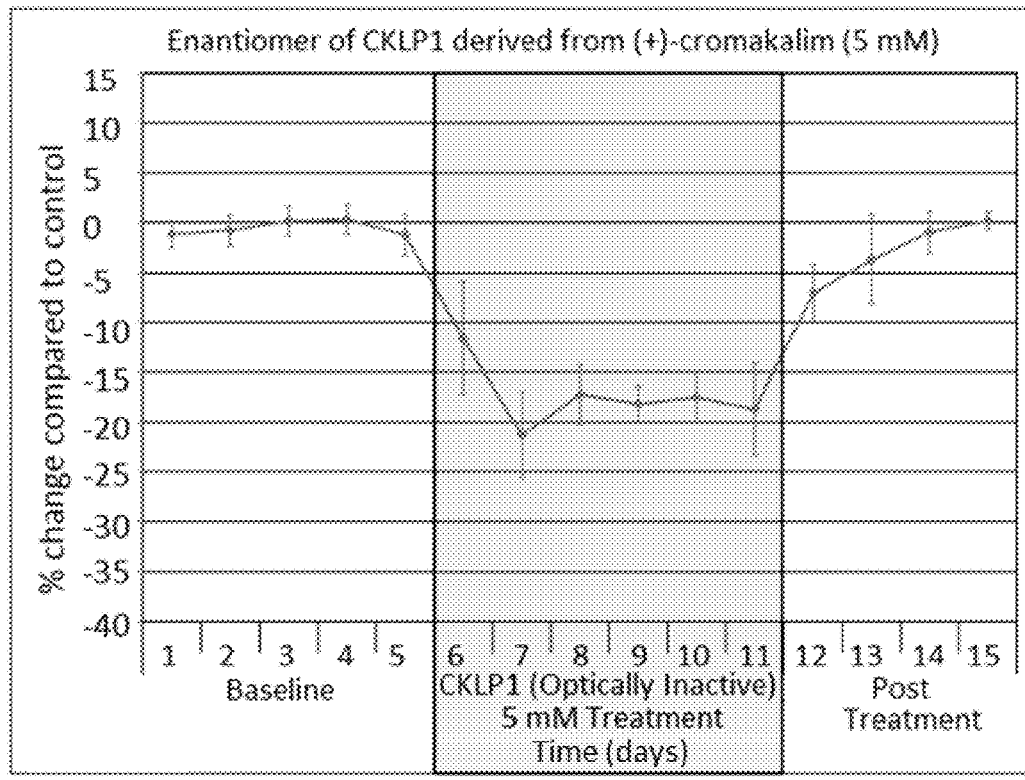
FIG. 5 is a graph showing the treatment with ent-CKLP1 (5 mM).
Figure 6:
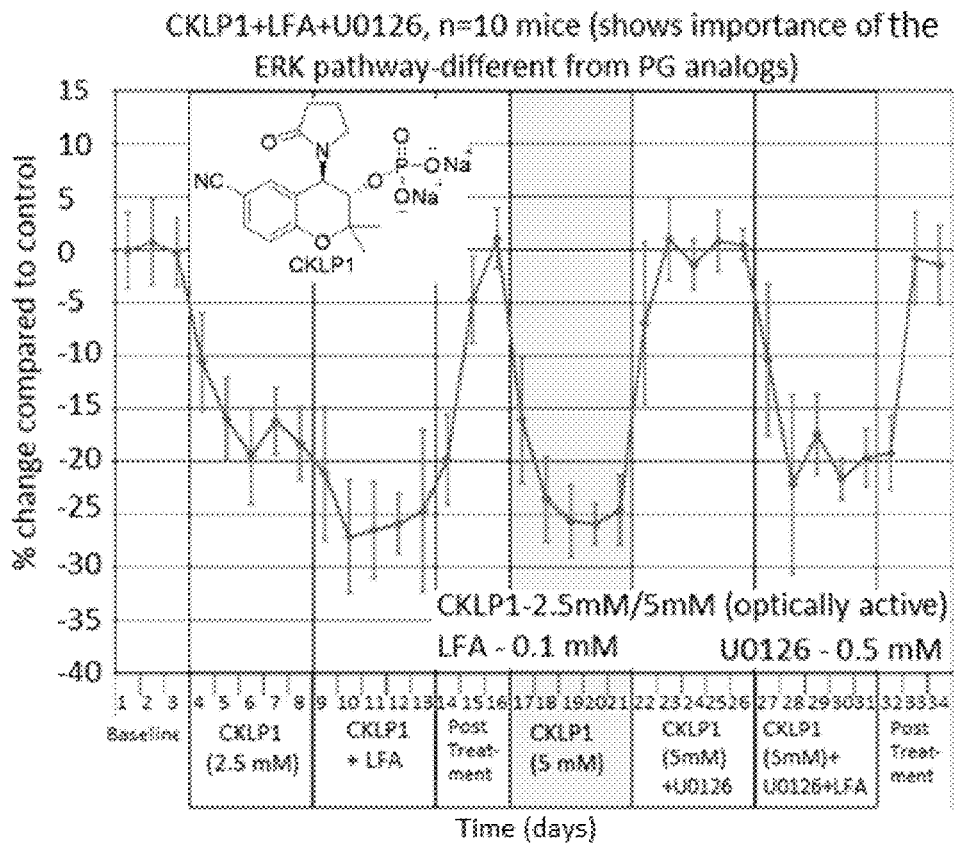
FIG. 6 is a graph showing the treatment of mice with CKLP1+LFA+U0126.

FIG. 3 is a graph showing the treatment with various forms of CKL. FIG. 4 is a graph showing the treatment of rabbits (n=5) with CKL-P1 in PBS, optically active isomer. FIG. 5 is a graph showing the treatment with ent-CKLP1 (5 mM). FIG. 6 is a graph showing the treatment of mice (n=10) with CKLP1+LFA+U0126 (shows importance of the ERK pathway-different from PG analogs). This suggests that CKLP1 works through the Erk1/2 signaling pathway. In the presence of Erk1/2 inhibitor U0126, CKLP1 is not able to lower pressure, while LFA can lower IOP (in mice).

Figure 7:
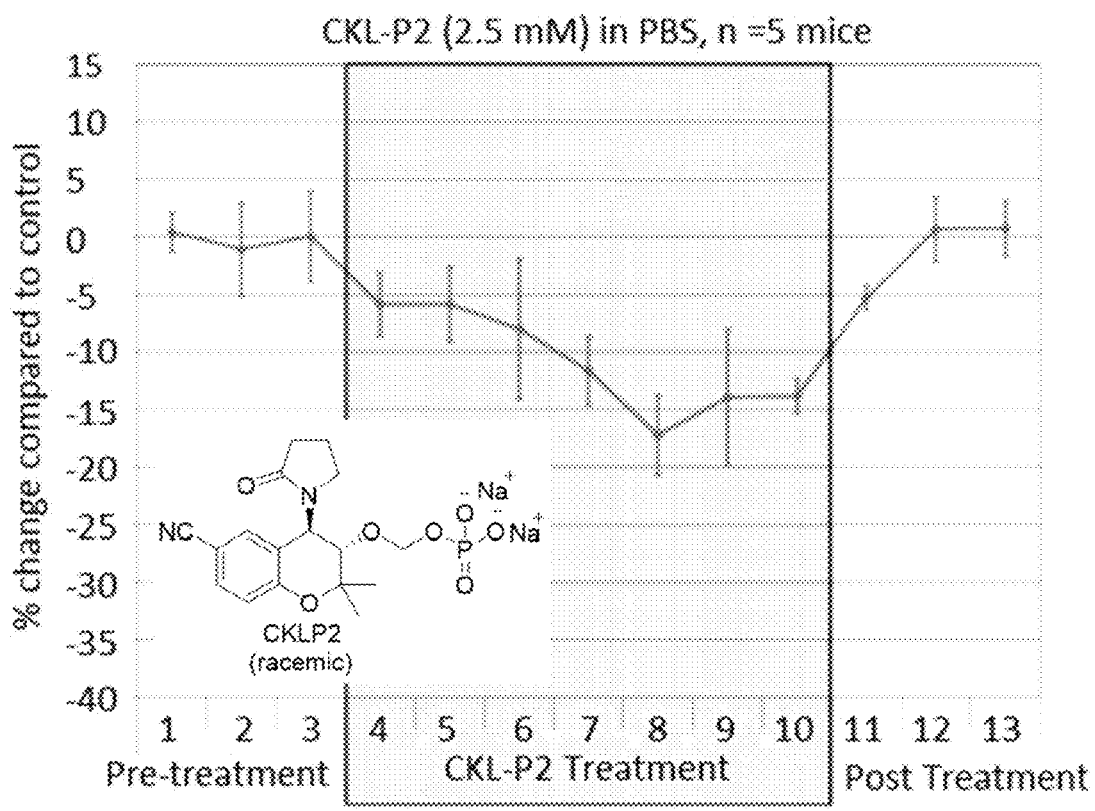
FIG. 7 is a graph showing the treatment of mice with CKL-P2 (2.5 mM) in PBS.

FIG. 7 is a graph showing the treatment of mice (n=5) with CKL-P2 (2.5 mM) in PBS.

Figure 8:
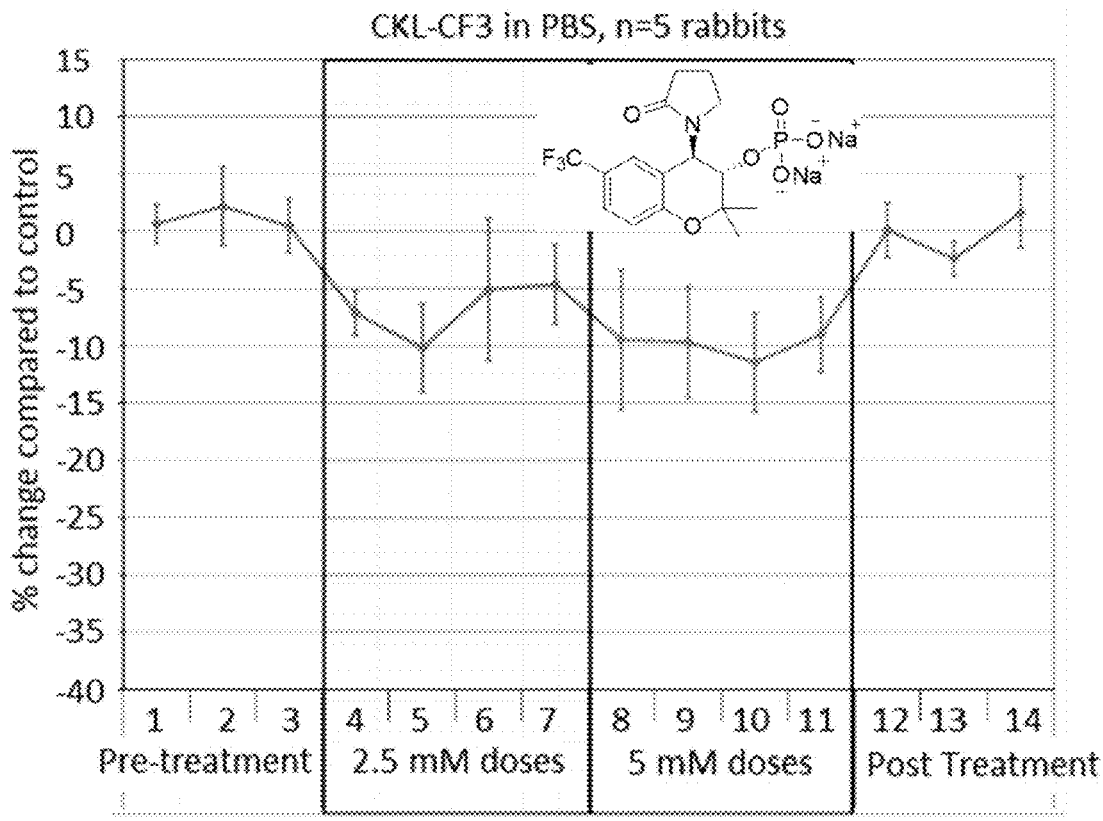
FIG. 8 is a graph showing the treatment of rabbits with CKL-CF3 in PBS.

FIG. 8 is a graph showing the treatment of rabbits (n=5) with CKL-CF3 in PBS.

Figure 9:
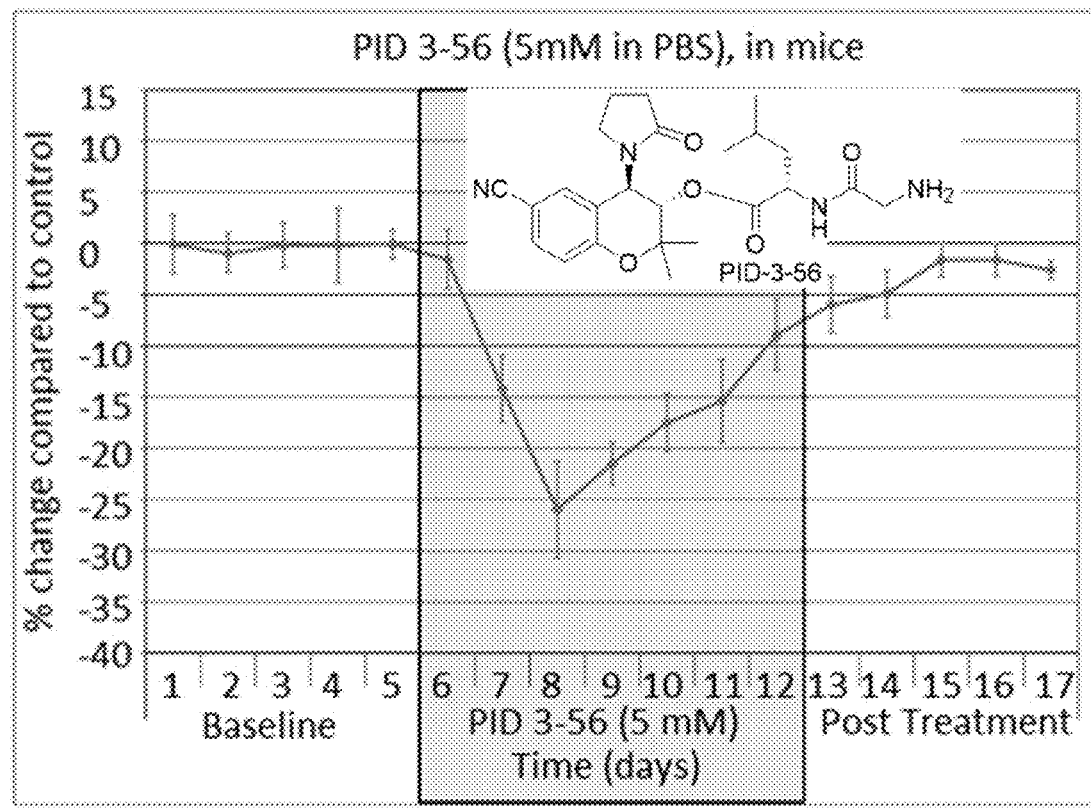
FIG. 9 is a graph showing the treatment of mice with PID 3-56 (5 mM in PBS).
Figure 10:
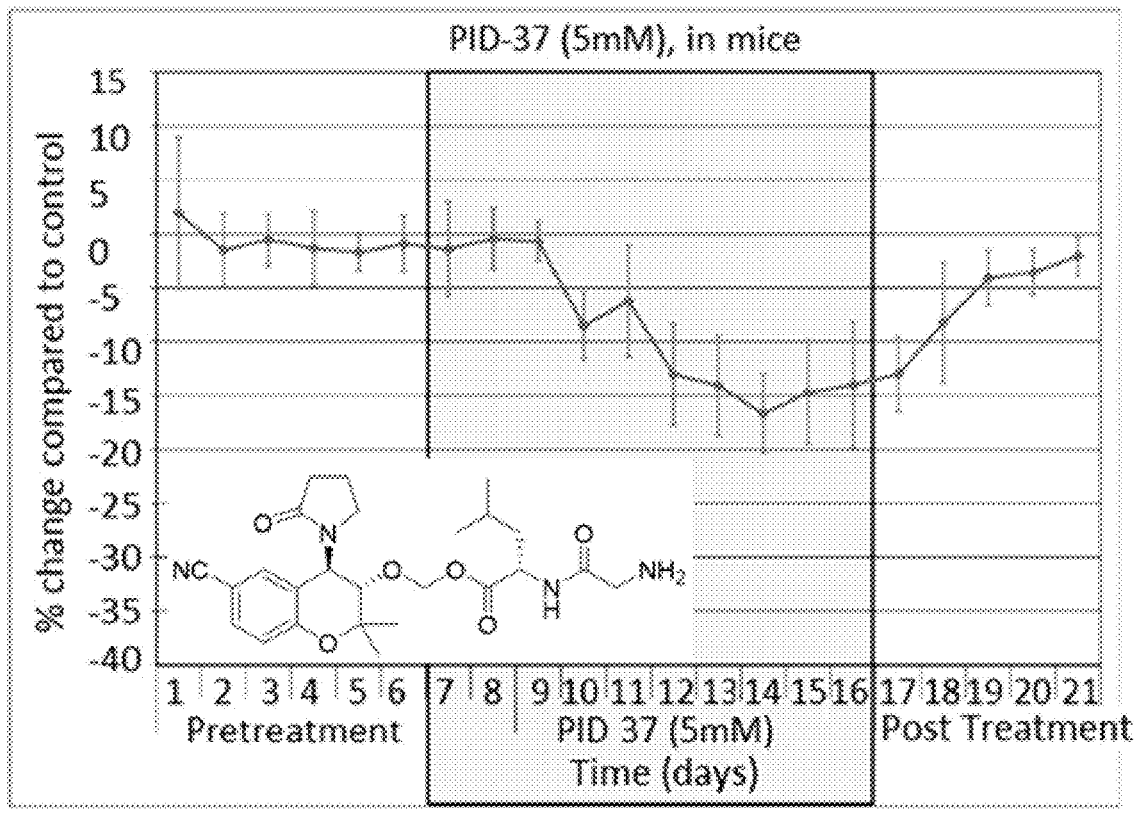
FIG. 10 is a graph showing the treatment of mice with PID-37 (5 mM).
Figure 11:
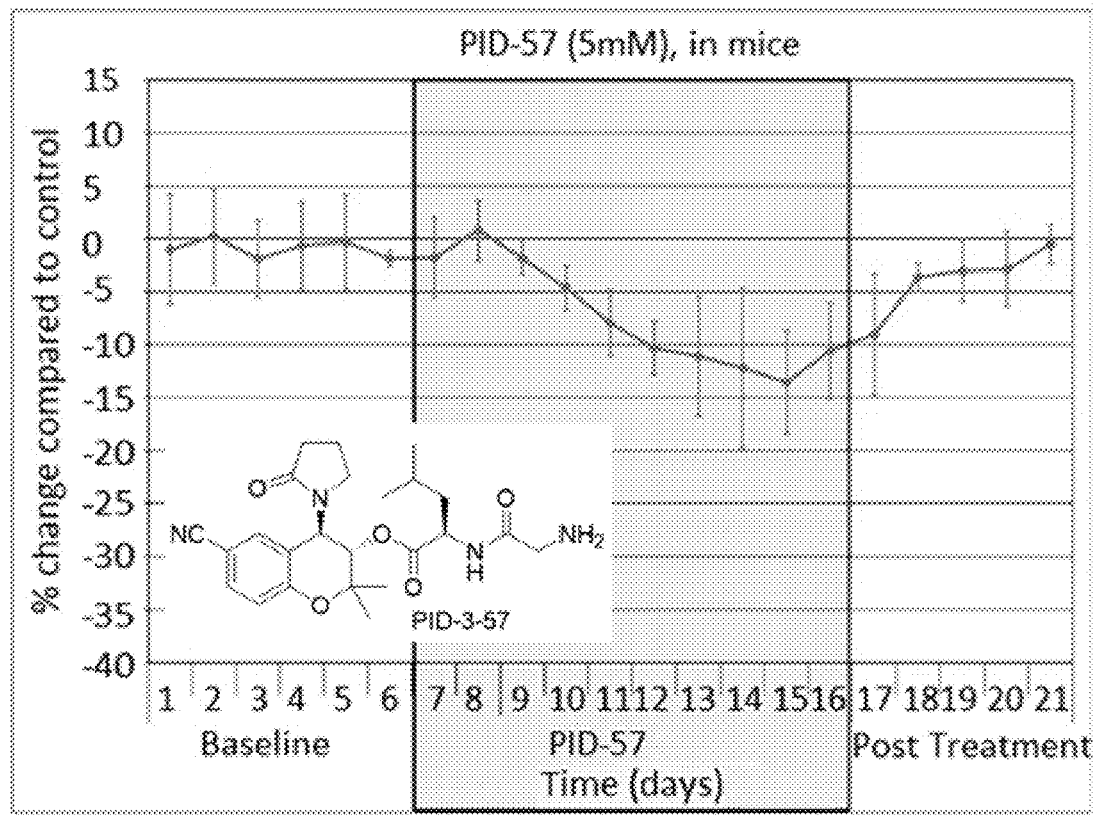
FIG. 11 is a graph showing the treatment of mice with PID-57 (5 mM).
Figure 12:
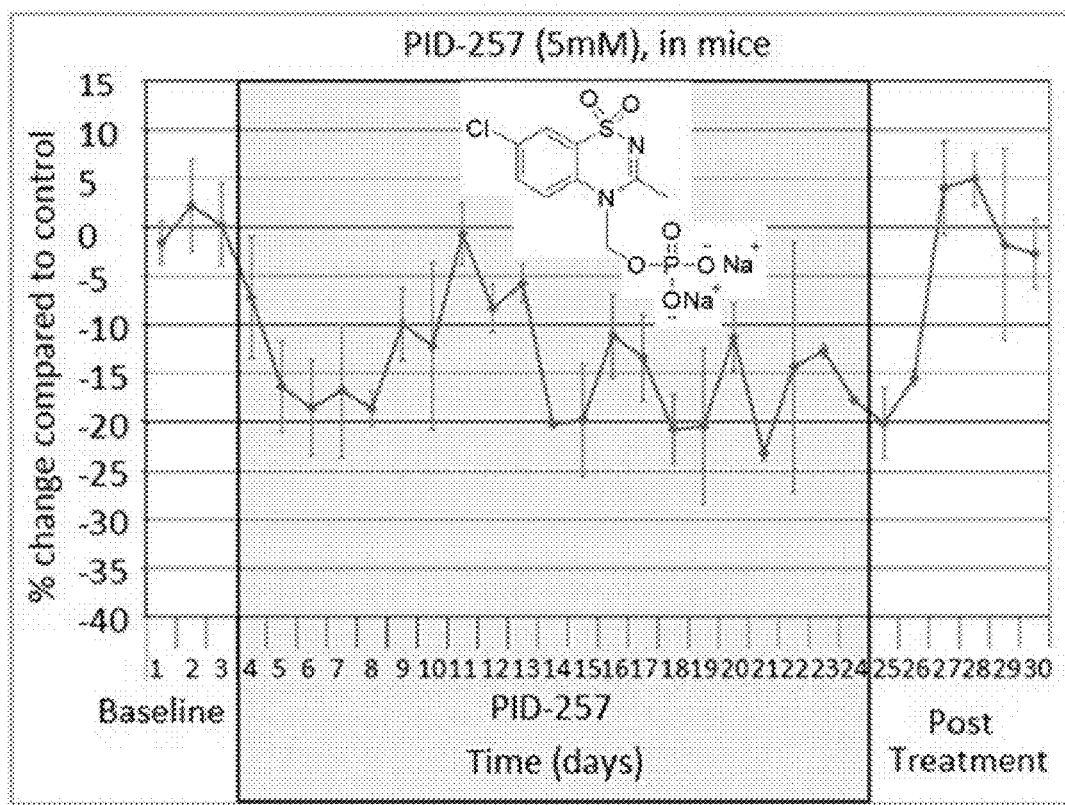
FIG. 12 is a graph showing the treatment of mice with PID-257 (5 mM).
Figure 13:
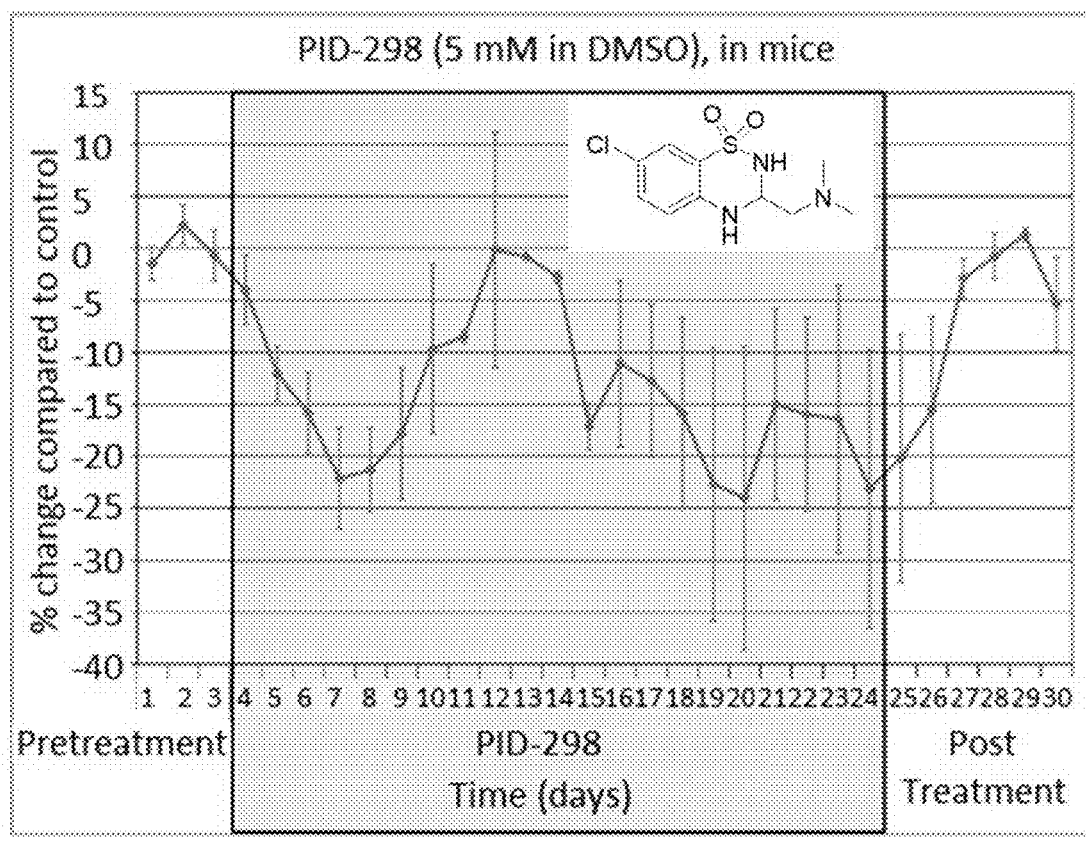
FIG. 13 is a graph showing the treatment of mice with PID-298 (5 mM in DMSO).
Figure 14:
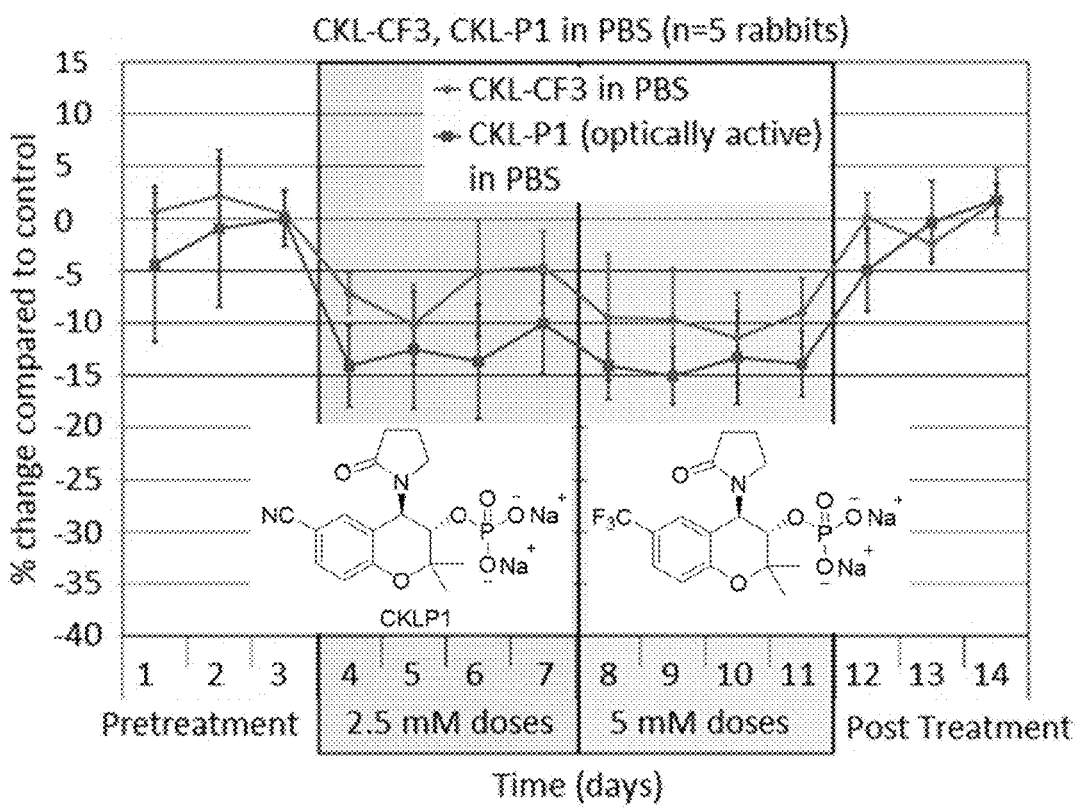
FIG. 14 is a graph showing the treatment of rabbits with CKL-CF3, CKL-P1 in PBS.

FIG. 9 is a graph showing the treatment of mice with PID 3-56 (5 mM in PBS). FIG. 10 is a graph showing the treatment of mice with PID-37 (5 mM). FIG. 11 is a graph showing the treatment of mice with PID-57 (5 mM). FIG. 12 is a graph showing the treatment of mice with PID-257 (5 mM). FIG. 13 is a graph showing the treatment of mice with PID-298 (5 mM in DMSO). FIG. 14 is a graph showing the treatment of rabbits (n=5) with CKL-CF3, CKL-P1 in PBS.

Figure 15:
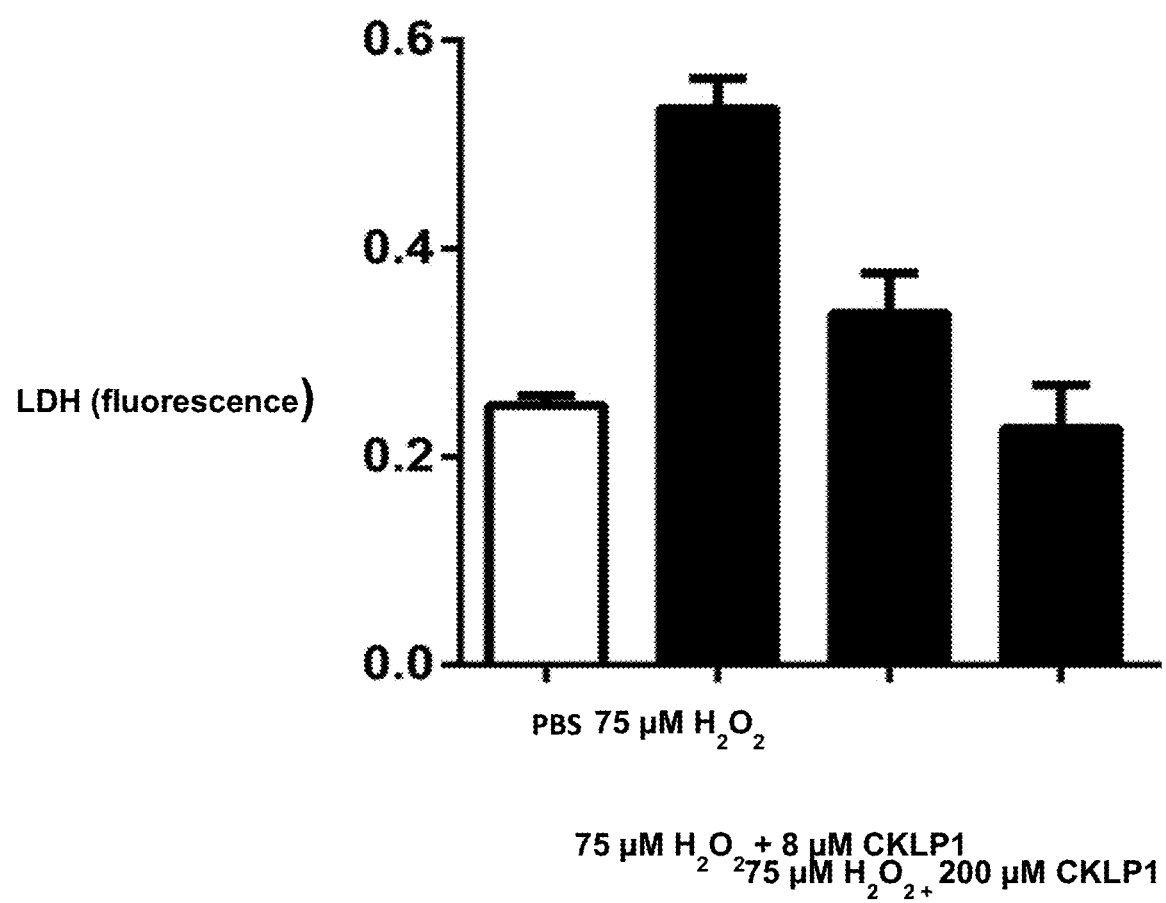
FIG. 15 is a graph showing CKLP1 inhibits $H_2O_2$ oxidative stress.

FIG. 15 is a graph showing CKLP1 inhibits $H_2O_2$ oxidative stress. The present invention also provides a CKLP1 composition used to treat neurons; a CKLP1 composition used for neuroprotection; a method of neuroprotection using a CKLP1 composition; a method of treating neurons using a CKLP1 composition; and methods and compositions for the treatment of ocular hypertension, blindness and loss of vision using a CKLP1 composition. The claimed CKLP1 composition provides neuroprotective properties. As seen in FIG. 15, rat cortical neurons were treated with 75 µM $H_2O_2$ for 24 hours with and without CKLP1 and the levels of lactate dehydrogenase were assayed. CKLP1 inhibited $H_2O_2$ oxidative stress in rat cortical neurons and in turn provides protection for the optic nerves. This is significant since current treatments for ocular hypertension do not protect the optic nerve, which is the site of damage and ultimate vision loss. Therefore, CKLP1 and other prodrugs (as disclosed herein) may represent the first in class treatment for glaucoma that can treat the main risk factor (elevated intraocular pressure) and also the sight of damage (optic nerve).

In another one embodiment, the present invention provides a series of prodrugs of levcromakalim conjugated to dipeptides. These dipeptides increase solubility and allow the prodrugs to be actively transported into the eye via oligopeptide transporters.

The present disclosure provides aqueous-soluble compositions for the treatment of glaucoma and/or reducing intraocular pressure in patients. One of the compositions is a benzopyrylium derivative which is soluble in aqueous solution. For example the composition has the structure:

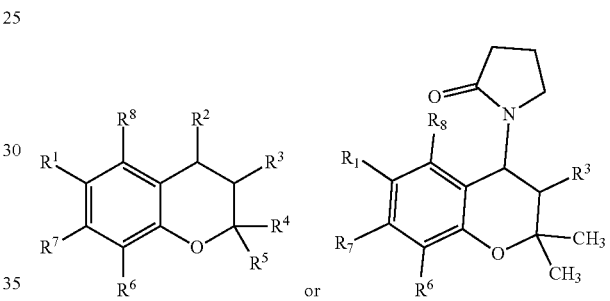

wherein $R^1$ is a protecting group and $R^2$-$R^5$ are functional groups as disclosed herein. $R^1$ may be a nitrile group, alkyl group, haloalkane group, fluoroalkane group, nitro group, amine group, carbonylalkyl group, sulfonyl group, or substituted sulfonyl group. For example R1 may be a —CN, —$CF_3$, —$CCF_2CF_3$, —$CF_2CF_3$, —$CF(CF_3)_2$, —$NO_2$, —$NH_2$, —$COCH_3$,

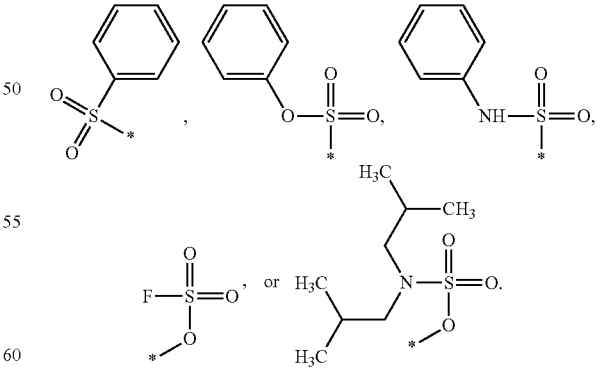

Although R2 is shown above as a substituted monocyclic heterocycle ring, R2 may be a $C_3$-$C_8$ member monocyclic heterocycle ring or a substituted $C_3$-$C_8$ member monocyclic heterocycle ring having one or more substitutions and/or hetero atoms. For example, $R^2$ may be

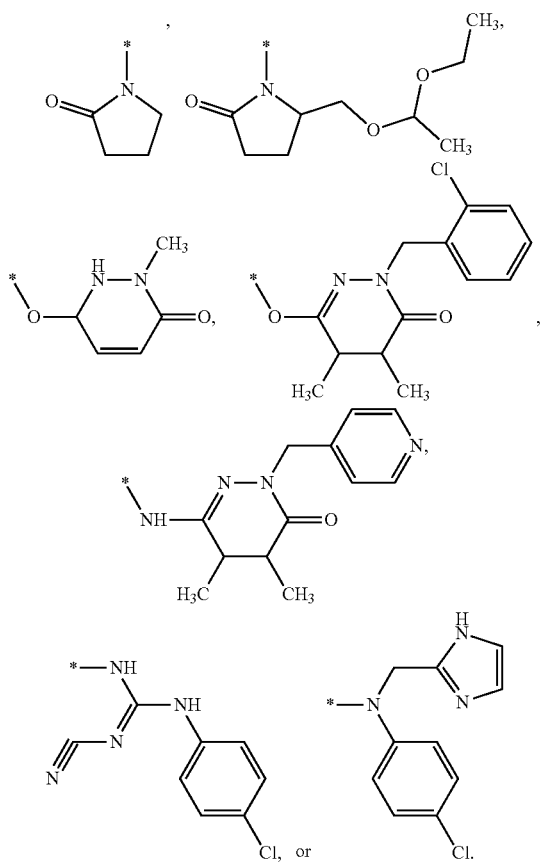

R3 is shown as a prodrug moiety and may be selected from:

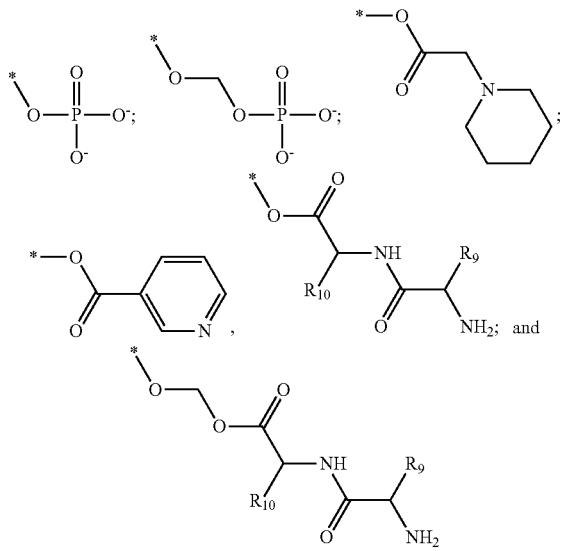

where R9 is a —H group (Gly) and R10 is a —CH$_2$CHCH$_3$CH$_3$ group (Leu); where R9 is a —H group (Gly) and R10 is a —CHCH$_3$CH$_3$ group (Val); and where R9 and R10 are both a —CHCH$_3$CH$_3$ group (Val). In addition, Leu can be in the D isomer configuration or the L isomer configuration. The amino acids may include any of the known amino acids, modified amino acids or non-naturally occurring amino acids and may include 1, 2, 3, 4, 5 or more amino acid residues.

Although R4 and R5 are independently shown above as alkyl group, R4 and R5 may independently be a —CH$_3$, —CH$_2$F, —OCH$_3$, —CF$_3$, —CCF$_2$CF$_3$, —CF$_2$CF$_3$, —CF(CF$_3$)$_2$, —NO$_2$, —NH$_2$, —COCH$_3$, or

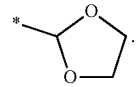

Although R6, R7 and R8 are independently shown above as hydrogens each may be an alkyl group, a substituted alkyl group, a nitrile functional group, an isothiocyanate group, an isocyanate functional group, a thiocyanate functional group, or a trifluoromethyl functional group.

The present disclosure provides aqueous-soluble compositions for the treatment of glaucoma and/or reducing intraocular pressure in patients. One of the composition is a benzopyrylium, levcromakalim or chroman (3,4-dihydro-2H-1-benzopyran) derivative which is soluble in aqueous solution. For example the composition has the structure:

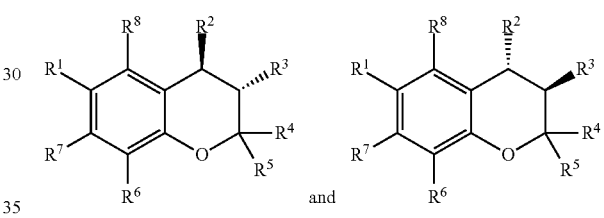

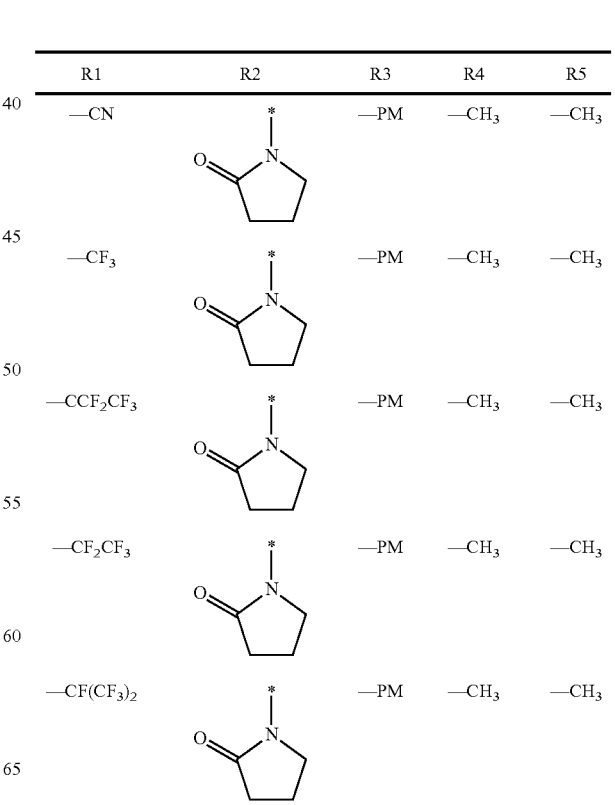

| R1 | R2 | R3 | R4 | R5 |
|---|---|---|---|---|
| ![phenylsulfonyl] | ![pyrrolidinone] | —PM | —CH₃ | —CH₃ |
| —NO₂ | ![pyrrolidinone] | —PM | —CH₃ | —CH₃ |
| —NO₂ | ![pyrrolidinone] | —PM | ![dioxolane] | —CH₃ |
| —CN | ![substituted pyrrolidinone] | —PM | —CH₃ | —CH₃ | wherein R6, R7 and R8 are H and PM is a prodrug moiety selected from:

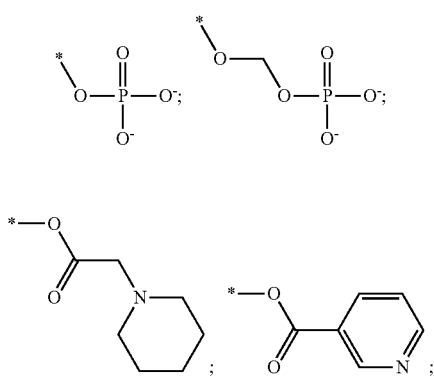

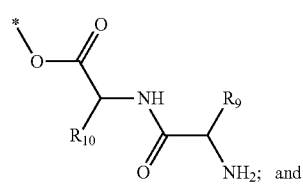

where R9 is a —H group (Gly) and R10 is a —CH₂CHCH₃CH₃ group (Leu); where R9 is a —H group (Gly) and R10 is a —CHCH₃CH₃ group (Val); and where R9 and R10 are both a —CHCH₃CH₃ group (Val). In addition, Leu can be in the D isomer configuration or the L isomer configuration. The amino acids may include any of the known amino acids, modified amino acids or non-naturally occurring amino acids and may include 1, 2, 3, 4, 5 or more amino acid residues. It is understood that R1-R8 may individually be a functional group selected from Alkyl, Substituted alkyl, alkenyl, alkoxy, alkoxyalkyl, carbonylalkyl, alkoxyphosphonic acid, alkylcarbonylalkoxy, cycloalkyl, cycloalkenyl, heterocycle, sulfur group, halogen, hydrogen, nitrogen group, —CN, —CH₂F, —CF₃, —CF₂CF₃, —CF₂CF₂CF₃.

Specific examples of the aqueous-soluble compositions for the treatment of glaucoma and/or reducing intraocular pressure in patients include composition having the structure:

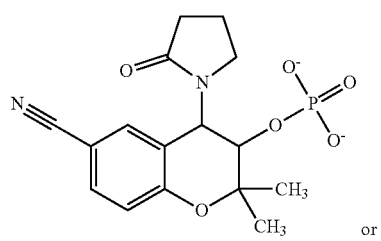 or

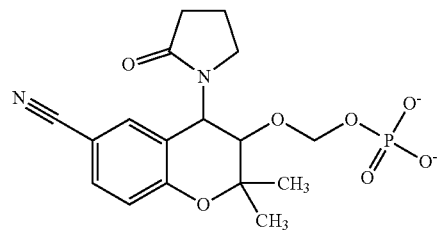

The compositions may have other protecting groups at the R1 location and still retain the aqueous solubility, e.g.

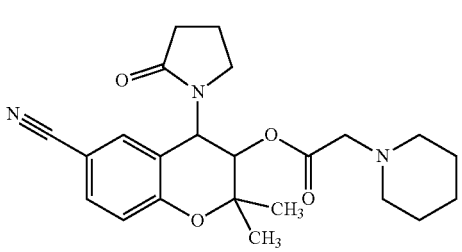 [SMILES: CC1(C)Oc2ccc(C#N)cc2C(N2CCCC2=O)C1OC(=O)CN1CCCCC1]

In addition, the protecting group may include one or more amino acids. The amino acids may include any of the known amino acids, modified amino acids or non-naturally occurring amino acids. The specific sequence or order of the amino acids may be varied as necessary:

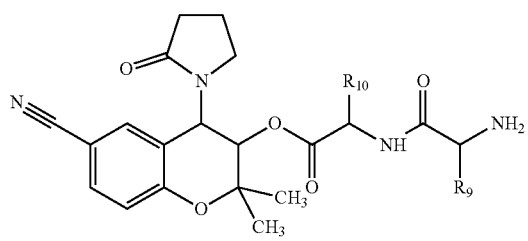

wherein R9 and R10 may independently be a —H; —CH$_2$CHCH$_3$CH$_3$; —CHCH$_3$CH$_3$; —CH$_3$; —CHCH$_3$CH$_2$CH$_3$; —CH$_2$(CH$_2$)$_3$NH$_2$; —CH$_2$CH$_2$SCH$_3$; —CH$_2$OH; or —CHOHCH$_3$. Specific levcromakalim derivative examples, include the levcromakalim structure where R$^1$ is a —H group (Gly) and R2 is a —CH$_2$CHCH$_3$CH$_3$ group (Leu); where R9 is a —H group (Gly) and R10 is a —CH$_2$CHCH$_3$CH$_3$ group (Leu); where R9 is a —H group (Gly) and R10 is a —CHCH$_3$CH$_3$ group (Val); and where R9 and R10 are both a —CHCH$_3$CH$_3$ group (Val). In addition, Leu can be in the D isomer configuration or the L isomer configuration. The amino acids may include any of the known amino acids, modified amino acids or non-naturally occurring amino acids and may include 1, 2, 3, 4, 5 or more amino acid residues.

In addition the linking bonds between the amino acid residues and the core levcromakalim derivative composition may be varied as necessary, e.g.,

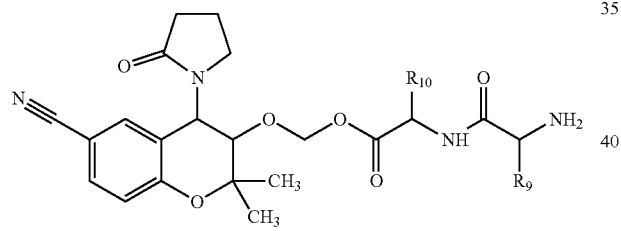

wherein R9 and R10 may independently be a —H; —CH$_2$CHCH$_3$CH$_3$; —CHCH$_3$CH$_3$; —CH$_3$; —CHCH$_3$CH$_2$CH$_3$; —CH$_2$(CH$_2$)$_3$NH$_2$; —CH$_2$CH$_2$SCH$_3$; —CH$_2$OH; or —CHOHCH$_3$. Specific levcromakalim derivative examples, include the levcromakalim structure where R$^1$ is a —H group (Gly) and R2 is a —CH$_2$CHCH$_3$CH$_3$ group (Leu); where R9 is a —H group (Gly) and R10 is a —CH$_2$CHCH$_3$CH$_3$ group (Leu); where R9 is a —H group (Gly) and R10 is a —CHCH$_3$CH$_3$ group (Val); and where R9 and R10 are both a —CHCH$_3$CH$_3$ group (Val). In addition, Leu can be in the D isomer configuration or the L isomer configuration. The amino acids may include any of the known amino acids, modified amino acids or non-naturally occurring amino acids and may include 1, 2, 3, 4, 5 or more amino acid residues.

The present disclosure provides aqueous-soluble compositions for the treatment of glaucoma and/or reducing intraocular pressure in patients. For example, the composition has the structure:

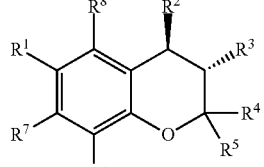

and

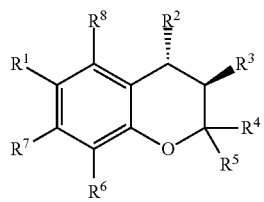

| R1 | R2 | R3 | R4 | R5 |
|---|---|---|---|---|
| —CN | 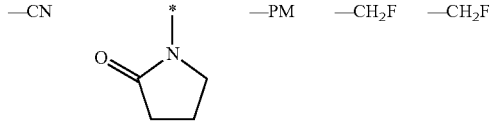 | —PM | —CH$_2$F | —CH$_2$F |
| —CF$_3$ | 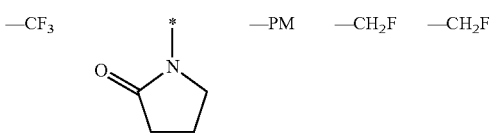 | —PM | —CH$_2$F | —CH$_2$F |
| —CCF$_2$CF$_3$ | 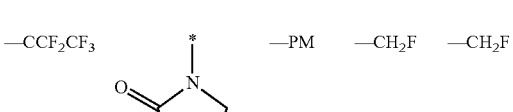 | —PM | —CH$_2$F | —CH$_2$F |
| —CF$_2$CF$_3$ | 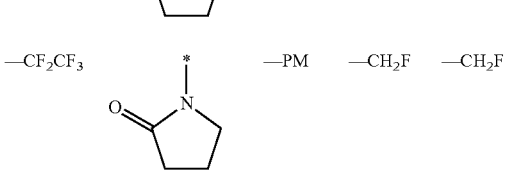 | —PM | —CH$_2$F | —CH$_2$F |

Wherein R6, R7 and R8 are H and PM is selected from:

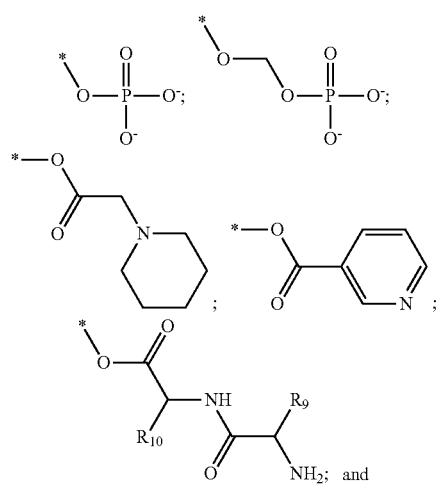

-continued

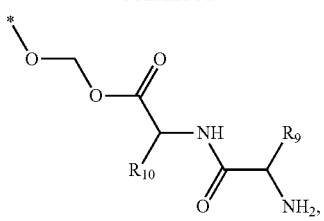

where R9 is a —H group (Gly) and R10 is a —CH₂CHCH₃CH₃ group (Leu); where R9 is a —H group (Gly) and R10 is a —CHCH₃CH₃ group (Val); and where R9 and R10 are both a —CHCH₃CH₃ group (Val). In addition, Leu can be in the D isomer configuration or the L isomer configuration. The amino acids may include any of the known amino acids, modified amino acids or non-naturally occurring aminoacids and may include 1, 2, 3, 4, 5or more amino acid residues.

The present disclosure also provides aqueous-soluble compositions for the treatment of glaucoma and/or reducing intraocular pressure inpatients. One of the composition is a benzopyrylium, levcromakalim or chroman (3,4-dihydro-2H-1-benzopyran) derivative which is soluble in aqueous solution. For example, the composition has the structure:

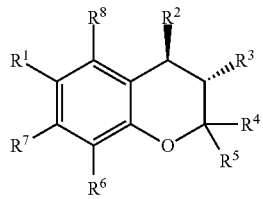

and

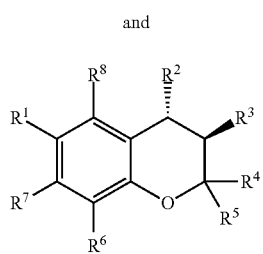

| R1 | R2 | R3 | R4 | R5 |
|---|---|---|---|---|
| —CN | 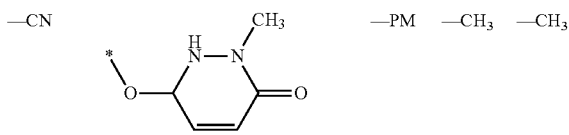 | —PM | —CH₃ | —CH₃ |
| —CN | 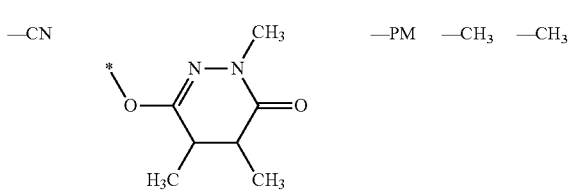 | —PM | —CH₃ | —CH₃ |

-continued

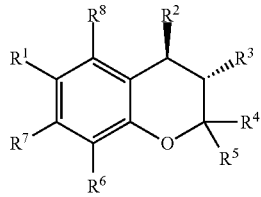

and

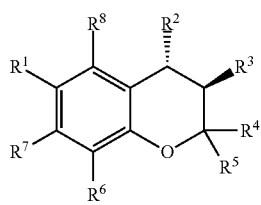

| R1 | R2 | R3 | R4 | R5 |
|---|---|---|---|---|
| —CN | 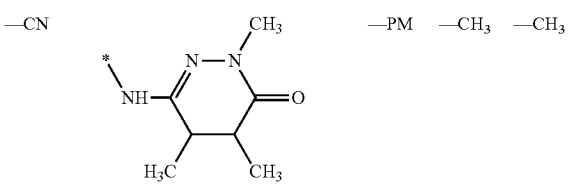 | —PM | —CH₃ | —CH₃ |
| —CN | 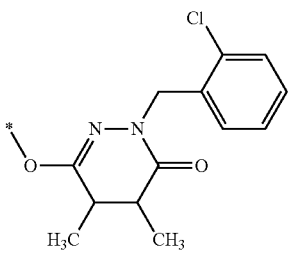 | —PM | —CH₃ | —CH₃ |
| —CN | 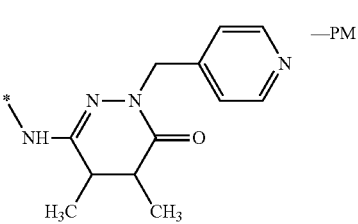 | —PM | —CH₃ | —CH₃ |

Wherein R6, R7 and R8 are H and PM is selected from:

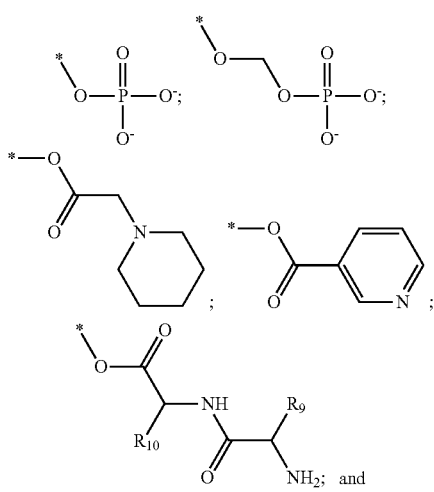

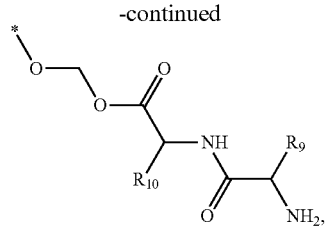

where R9 is a —H group (Gly) and R10 is a —CH₂CHCH₃CH₃ group (Leu); where R9 is a —H group (Gly) and R10 is a —CHCH₃CH₃ group (Val); and where R9 and R10 are both a —CHCH₃CH₃ group (Val). In addition, Leu can be in the D isomer configuration or the L isomer configuration. The amino acids may include any of the known amino acids, modified amino acids or non-naturally occurring amino acids and may include 1, 2, 3, 4, 5 or more amino acid residues.

The present disclosure provides aqueous-soluble compositions for the treatment of glaucoma and/or reducing intraocular pressure in patients. For example, the composition has the structure:

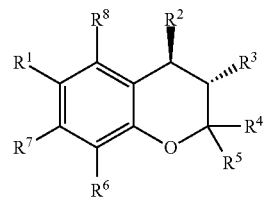

and

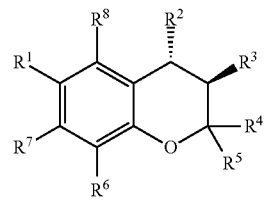

| R1 | R2 | R3 | R4 | R5 |
|---|---|---|---|---|
| —CN | 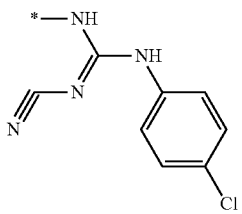 | —PM | —CH₃ | —CH₃ |
| —NH₂ | 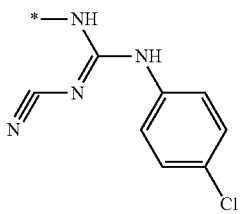 [SMILES: *N/C(=N\C#N)Nc1ccc(Cl)cc1] | —PM | —OCH₃ | —OCH₃ |

| R1 | R2 | R3 | R4 | R5 |
|---|---|---|---|---|
| 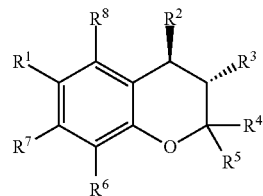 | 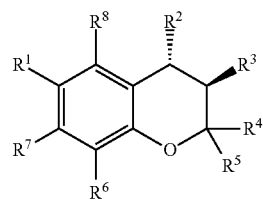 | —PM | —CH$_3$ | —CH$_3$ |
|  | 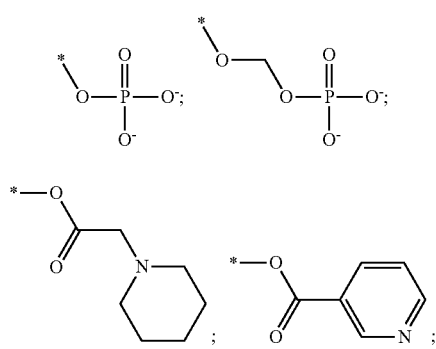 | —PM | —CH$_3$ | —CH$_3$ |

Wherein R6, R7 and R8 are H and PM is selected from:

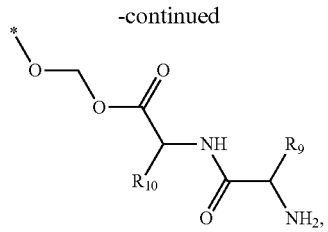

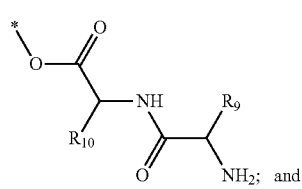

where R9 is a —H group (Gly) and R10 is a —CH$_2$CHCH$_3$CH$_3$ group (Leu); where R9 is a —H group (Gly) and R10 is a —CHCH$_3$CH$_3$ group (Val); and where R9 and R10 are both a —CHCH$_3$CH$_3$ group (Val). In addition, Leu can be in the D isomer configuration or the L isomer configuration. The amino acids may include any of the known amino acids, modified amino acids or non-naturally occurring amino acids and may include 1, 2, 3, 4, 5 or more amino acid residues.

The present disclosure provides aqueous-soluble compositions for the treatment of glaucoma and/or reducing intraocular pressure in patients. For example, the composition has the structure:

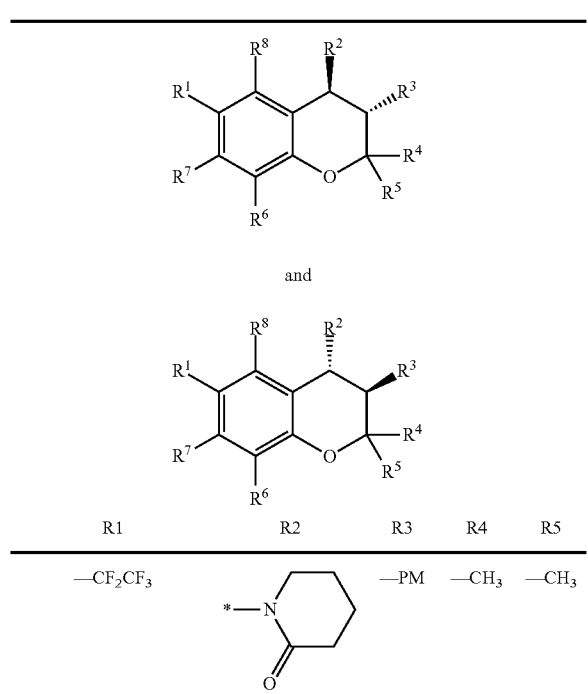

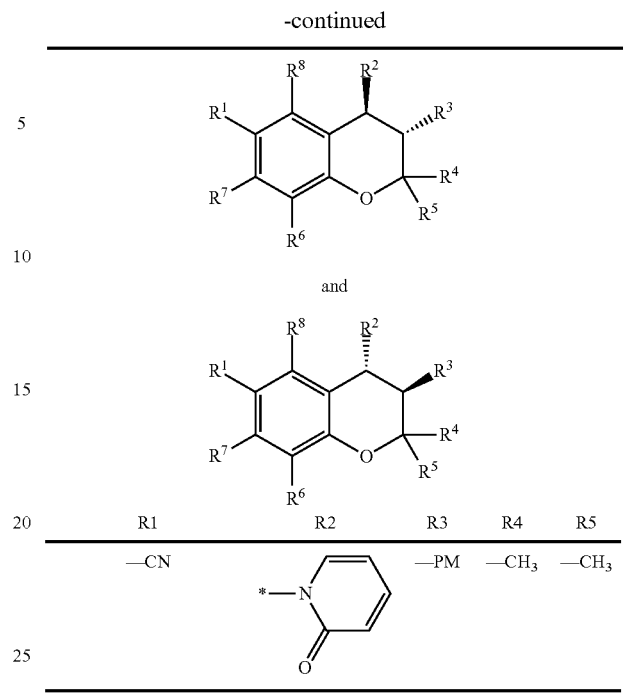

Wherein R6, R7 and R8 are H and R3 PM is selected from:

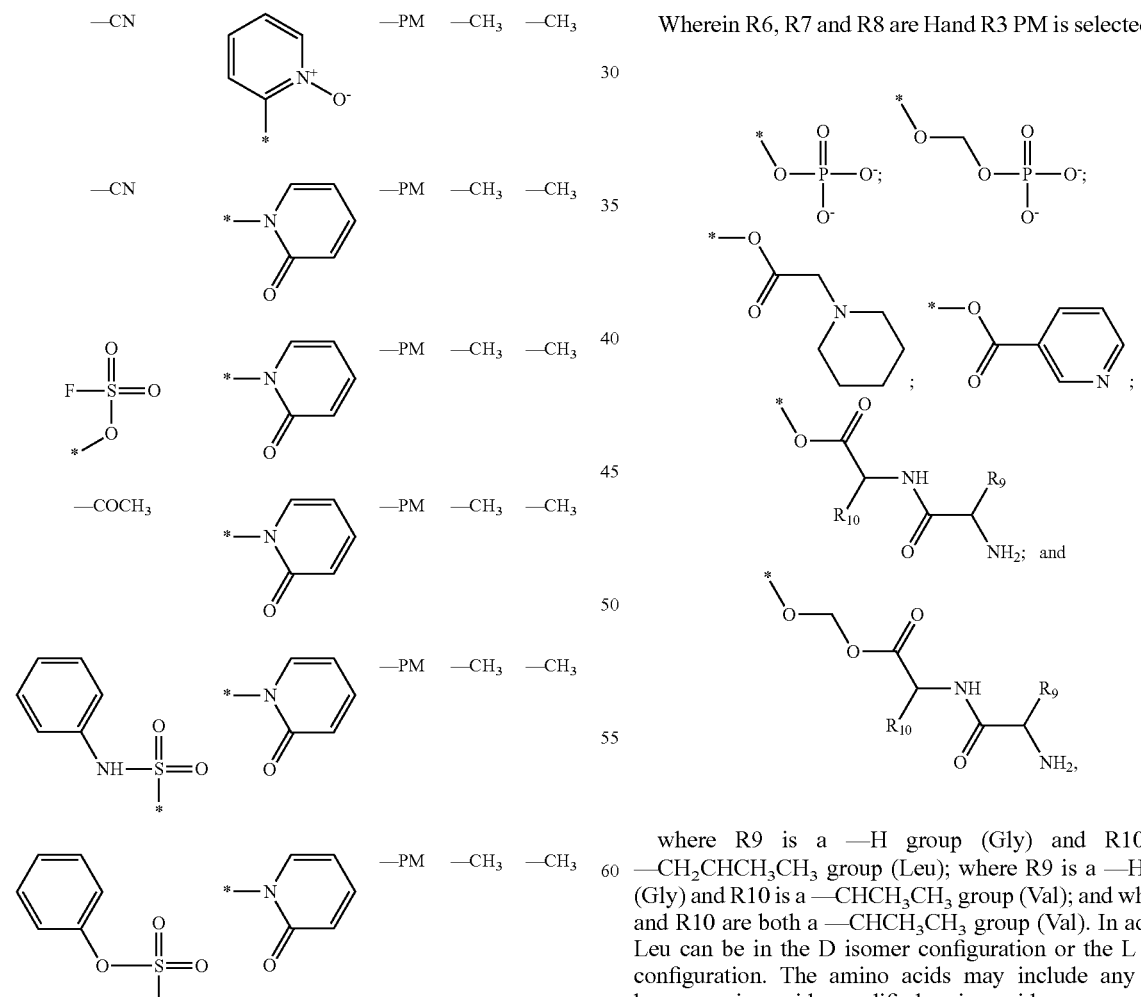

where R9 is a —H group (Gly) and R10 is a —CH$_2$CHCH$_3$CH$_3$ group (Leu); where R9 is a —H group (Gly) and R10 is a —CHCH$_3$CH$_3$ group (Val); and where R9 and R10 are both a —CHCH$_3$CH$_3$ group (Val). In addition, Leu can be in the D isomer configuration or the L isomer configuration. The amino acids may include any of the known amino acids, modified amino acids or non-naturally occurring amino acids and may include 1, 2, 3, 4, 5 or more amino acid residues.

The present disclosure provides aqueous-soluble compositions for the treatment of glaucoma and/or reducing intraocular pressure in patients. For example the composition has the structure:
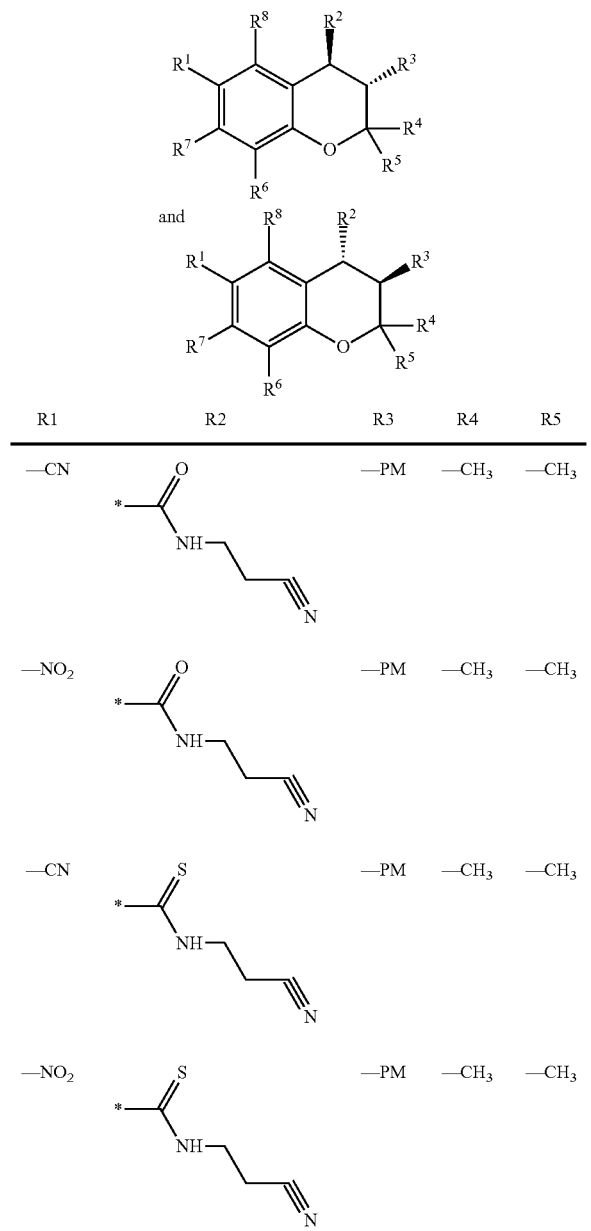
Wherein R6, R7 and R8 are H and PM is selected from:

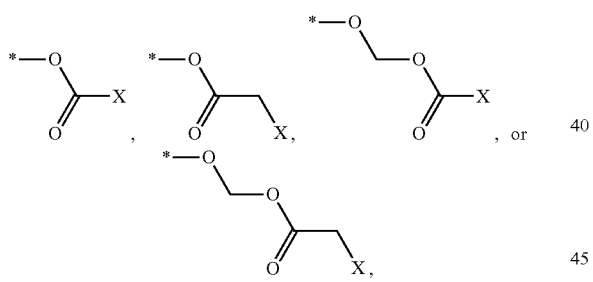

where R9 is a —H group (Gly) and R10 is a —CH$_2$CHCH$_3$CH$_3$ group (Leu); where R9 is a —H group (Gly) and R10 is a —CHCH$_3$CH$_3$ group (Val); and where R9 and R10 are both a —CHCH$_3$CH$_3$ group (Val). In addition, Leu can be in the D isomer configuration or the L isomer configuration. The amino acids may include any of the known amino acids, modified amino acids or non-naturally occurring amino acids and may include 1, 2, 3, 4, 5 or more amino acid residues. It is understood that R1-R8 may individually be a functional group selected from Alkyl, Substituted alkyl, alkenyl alkoxy, alkoxyalkyl, carbonylalkyl, alkoxyphosphonic acid, alkylcarbonylalkoxy, cycloalkyl, cycloalkenyl, heterocycle, sulfur group, halogen, hydrogen, nitrogen group, —CN, —CH$_2$F, —CF$_3$, —CF$_2$CF$_3$, —CF$_2$CF$_2$CF$_3$. In addition, other prodrug moiety or protecting groups may be used:

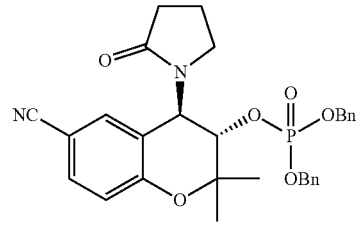 [SMILES: CC1(C)Oc2ccc(C#N)cc2[C@@H](N2CCCC2=O)[C@@H]1OP(=O)(OCc1ccccc1)OCc1ccccc1]

where X may be a Alkyl, Substituted alkyl, C$_3$-C$_8$ monocyclic cycloalkyl, C$_3$-C$_8$ monocyclic cycloalkenyl, 3- to 7-membered monocyclic heterocycle, 3- to 7-membered monocyclic heterocycle, e.g., azetidine, azete, oxetane, oxete, thietane, thiete, diazetidine, dioxetane, dioxete, pyrrolidine, pyrrole, tetrahydrofuran, furan, thiolane, thiophene, imidazolidine, imidazole, pyrazolidine, pyrazole, oxazolidine, oxazole, isoxazolidine, isoxazole, isothiazolidine, isothiazole, thiazolidine, thiazole, or substituted variations thereof.

$^1$H NMR and $^{13}$C NMR Spectra were recorded on a Bruker 400 spectrometer. The $^1$H NMR data are reported as follows: chemical shift in parts per million downfield of tetramethylsilane (TMS), multiplicity (s=singlet, bs=broad singlet, d=doublet, t=triplet, q=quartet, quint=quintet and m=multiplet), coupling constant (Hz), and integrated value. Coupling constants listed as J$_{31P}$ disappeared when $^1$H NMR spectra were taken with $^{31}$P decoupling. The $^{13}$C NMR spectra were measured with complete proton decoupling. $^{31}$P NMR spectra taken for compound characterization were measured with complete proton decoupling and were referenced to 85% phosphoric acid, which was added to the NMR tube in a sealed capillary tube. LC/MS analysis was carried out using a BEH C$_{18}$ column (2.1 mm×50 mm, 5 um) on a Waters Acquity UPLC system with a Waters ZQ mass detector.

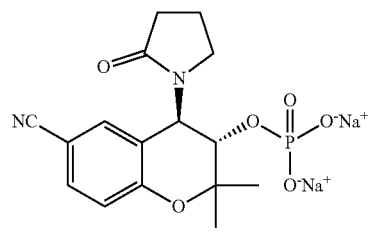

To a stirred suspension of cromakalim (50 mg, 0.175 mmol) in CH$_2$Cl$_2$ (5 mL) was added 0.45 M tetrazole in acetonitrile (3.9 mL, 1.76 mmol) followed by dibenzyl N,N-dimethylphosphoramidite (0.200 mL, 0.75 mmol). The reaction mixture was stirred at rt for 2.5 h. After cooling the mixture in an ice bath, THF (5 mL) was added, followed by drop wise addition of 30% H$_2$O$_2$ (1 mL). After stirring for 5 min., saturated aqueous Na$_2$S$_2$O$_3$ (30 mL) was added slowly. The mixture was diluted with water (50 mL) and extracted with CH$_2$Cl$_2$ (2×50 mL). The combined organic layers were dried (Na$_2$SO$_4$), filtered, and concentrated under reduced pressure. Purification by flash chromatography (35% ethyl acetate/hexanes) on silica gel followed by a second flash chromatography (60% ethyl acetate/hexanes) on silica gel furnished 89.8 mg product (94% yield) as a clear colorless oil.

To a solution of dibenzyl ((3S,4R)-6-cyano-2,2-dimethyl-4-(2-oxopyrrolidin-1-yl)chroman-3-yl) phosphate (65.5 mg, 0.120 mmol) in dry CH$_2$Cl$_2$ (3 mL) was added TMSBr (53 μL, 0.40 mmol) by syringe. After stirring for 6 hours, the reaction mixture was concentrated under reduced pressure. The resulting residue was purified by chromatography (0% acetonitrile/20 mM triethylammonium acetate buffer to 100% acetonitrile, C$_{18}$ column) to yield 53.5 mg white solid after lyophilization. To prepare the sodium salt, a 1 cm wide column was filled with 12 cm of DOWEX 50W2 (50-100 mesh) ion exchange resin. The column was prepared by sequentially washing with 1:1 acetonitrile/water, 1M aqueous NaHCO$_3$, water, and then finally 1:1 acetonitrile/water. The reaction product was dissolved in 1:1 acetonitrile/water and loaded onto the column, which was eluted with 1:1 acetonitrile/water. The product containing fractions were lyophilized to furnish as a white solid (40.9 mg, 83% yield).

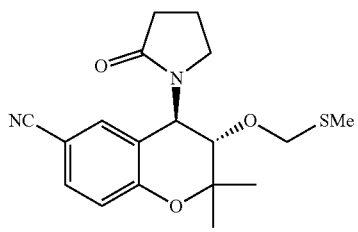 [SMILES: CSCO[C@H]1[C@H](N2CCCC2=O)c2cc(C#N)ccc2OC1(C)C]

To a solution of cromakalim (188.2 mg, 0.657 mmol) in DMSO (10 mL) was added acetic anhydride (10 mL) and acetic acid (6 mL). After stirring at rt for 24 hours, the reaction mixture was diluted with water (400 mL) and carefully neutralized with solid NaHCO$_3$. The mixture was extracted with ethyl acetate (3×400 mL). The organic layers were then each further extracted with water (400 mL), combined, dried (Na$_2$SO$_4$), filtered, and concentrated under reduced pressure. Purification by flash chromatography (30% to 100% ethyl acetate/hexanes) on silica gel furnished 202.5 mg of product (89% yield) as a white solid.

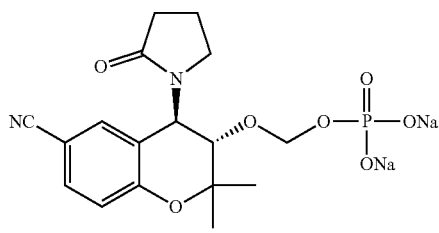

To a stirred suspension of (3S,4R)-2,2-dimethyl-3-((methylthio)methoxy)-4-(2-oxopyrrolidin-1-yl)chromane-6-carbonitrile (30.8 mg, 0.089 mmol), phosphoric acid (74.1 mg, 0.756 mmol) and 4 Å molecular sieves (239 mg) in THF (3 mL) at 0° C., was added a solution of N-iodosuccinimide (32.9 mg, 0.146 mmol) in THF (1 mL). After warming to rt over 2 hours, a TLC showed starting material remaining, so additional NIS was added (37 mg, 0.164 mmol). An hour later, the mixture was decanted to remove the sieves. Aqueous sodium thiosulfate was added until the color disappeared and then 0.5 mL of 1 M triethylammonium acetate buffer was added. The THF was removed under reduced pressure and the resulting residue purified by chromatography (0% acetonitrile/20 mM triethylammonium acetate buffer to 100% acetonitrile, C18 column) to yield 13.4 mg of brown solid after lyophilization. To prepare the sodium salt, a 1 cm wide column was filled with 12 cm of DOWEX 50W2 (50-100 mesh, strongly acidic) ion exchange resin. The column was prepared by sequentially washing with 1:1 acetonitrile/water, 1M aqueous NaHCO$_3$ (lots of gas evolution), water, and then finally 1:1 acetonitrile/water. The reaction product was dissolved in 1:1 acetonitrile/water and loaded onto the column, which was eluted with 1:1 acetonitrile/water. The product containing fractions were lyophilized to furnish CKLP2 as a white solid (7.7 mg, 20% yield).

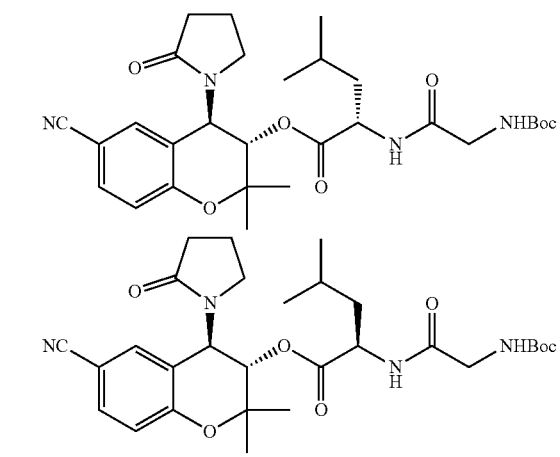

A suspension of leveromakalim (80.6 mg, 0.281 mmol), DMAP (308.9 mg, 2.53 mmol), and Boc-gly-leu-OH (334.7 mg, 1.16 mmol) was stirred for 10 min. in DCM (5 mL). HATU (473.7 mg, 1.25 mmol) was added and the mixture stirred at rt. After 24 h., the solvent was removed under reduced pressure and the resulting residue was purified by chromatography (25% to 75% ethyl acetate/hexanes) on silica gel to furnish 103 mg of Boc-epimer 1, followed by 31.9 mg of Boc-epimer 2, both as waxy white solids. Epimer 1:

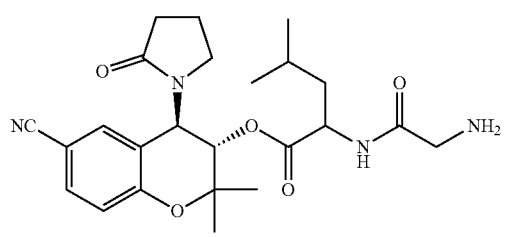 [SMILES: CC(C)CC(NC(=O)CN)C(=O)O[C@H]1[C@H](N2CCCC2=O)c2cc(C#N)ccc2OC1(C)C]

Boc-epimer 1 (26 mg, 0.047 mmol) was dissolved in 4 M HCl in dioxane (5 mL) and stirred for 30 min. The reaction mixture was concentrated under reduced pressure. The resulting residue was purified by chromatography (10% acetonitrile/water with 0.1% formic acid to 100% acetonitrile, C$_{18}$ column) to yield 5.0 mg after lyophilization (21% yield) as a formic acid salt. Epimer 2:

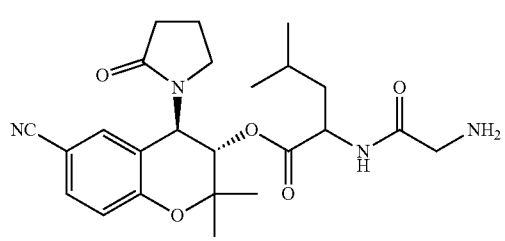 [SMILES: CC(C)CC(NC(=O)CN)C(=O)O[C@H]1[C@H](N2CCCC2=O)c2cc(C#N)ccc2OC1(C)C]

Boc-epimer 2 (18.5 mg, 0.033 mmol) was dissolved in 4 M HCl in dioxane (5 mL) and stirred for 30 min. The reaction mixture was concentrated under reduced pressure. The resulting residue was purified by chromatography (10% acetonitrile/water with 0.1% formic acid to 100% acetonitrile, C18 column) to yield 4.1 mg after lyophilization (25% yield) as a formic acid salt.

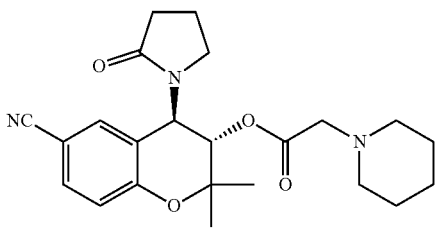 [SMILES: CC1(C)Oc2ccc(C#N)cc2[C@@H](N2CCCC2=O)[C@@H]1OC(=O)CN1CCCCC1]

A suspension of leveromakalim (28.7 mg, 0.100 mmol), DMAP (116.9 mg, 0.957 mmol), and piperidin-1-yl-acetic acid (49.0 mg, 0.342 mmol) was stirred for 10 min. in DCM (2 mL). HATU (119.8 mg, 0.315 mmol) was added and the mixture stirred at rt for 72 h. The reaction mixture was filtered and the solvent was removed under reduced pressure. The resulting residue purified by chromatography (10% to 100% ethyl acetate/hexanes) on a RediSep Rf amine column to furnish 39.5 mg of product (96% yield) as a white solid.

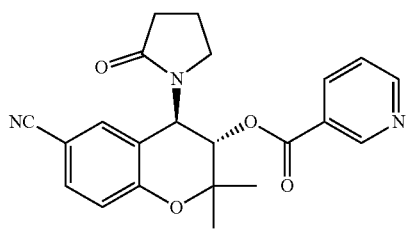 [SMILES: CC1(C)Oc2ccc(C#N)cc2[C@@H](N2CCCC2=O)[C@@H]1OC(=O)c1cccnc1]

A suspension of levcromakalim (26.1 mg, 0.091 mmol), DMAP (125.9 mg, 1.03 mmol), and nicotinic acid (42.4 mg, 0.344 mmol) was stirred for 10 min. in DCM (2 mL). HATU (109.8 mg, 0.289 mmol) was added and the mixture stirred at rt. After 24 h., the solvent was removed under reduced pressure and the resulting residue was purified by chromatography (15% to 100% ethyl acetate/hexanes) on a RediSep Rf amine column, followed by a second flash chromatography (75% to 100% ethyl acetate/hexanes) on silica gel to furnish 34.6 mg product (97% yield) as a waxy white solid.

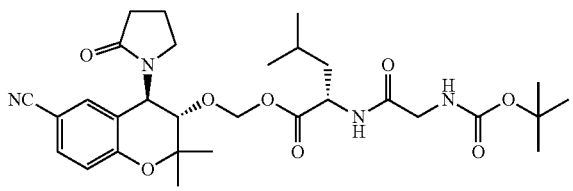 [SMILES: CC(C)C[C@H](NC(=O)CNC(=O)OC(C)(C)C)C(=O)OCO[C@H]1[C@H](N2CCCC2=O)c2cc(C#N)ccc2OC1(C)C]

To a solution of (3S,4R)-2,2-dimethyl-3-((methylthio)methoxy)-4-(2-oxopyrrolidin-1-yl)chromane-6-carbonitrile (57.0 mg, 0.165 mmol) in DCE (1.5 mL) was added sulfuryl chloride (0.95 mL of 1 M in DCM solution, 0.95 mmol). After stirring for 90 min., the solvent was removed under reduced pressure and the resulting residue was left under vacuum for 10 min. The residue was then dissolved in acetonitrile (1 mL) and a solution of Boc-Gly-Leu-OH (110.8 mg, 0.384 mmol) in acetonitrile (3 mL) added by syringe. After 3 h., the solvent was removed under reduced pressure and the resulting residue was purified by chromatography (30% to 100% ethyl acetate/hexanes) on silica gel to furnish 96.1 mg of product as a white solid (99% yield).

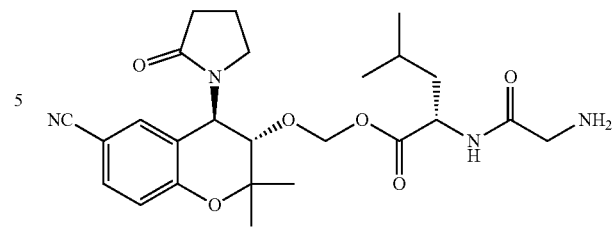

Chemical Formula: $C_{25}H_{34}N_4O_6$
Exact Mass: 486.247B
Molecular Weight: 486.5607

The material from the previous section (42.4 mg, 0.072 mmol) was dissolved in 4 M HCl in dioxane (2 mL) and stirred for 30 min. The reaction mixture was concentrated under reduced pressure. The resulting residue was washed with diethyl ether, which was then discarded. The remaining material was purified by chromatography (10% acetonitrile/water to 100% acetonitrile, $C_{18}$ column). The product containing fractions were lyophilized after a small amount of dilute HCl was added to them. 8.8 mg white solid (23% yield) as an HCl salt.

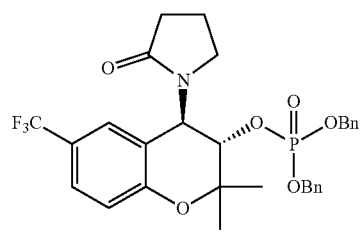 [SMILES: CC1(C)Oc2ccc(C(F)(F)F)cc2[C@@H](N2CCCC2=O)[C@@H]1OP(=O)(OCc1ccccc1)OCc1ccccc1]

To a stirred suspension of the $CF_3$-analog of cromakalim (161.1 mg, 0.489 mmol) in $CH_2Cl_2$ (15 mL) was added 0.45 M tetrazole in acetonitrile (11.5 mL, 5.18 mmol) followed by dibenzyl N,N-dimethylphosphoramidite (0.600 mL, 2.26 mmol). The reaction mixture was stirred at rt for 4 h. A TLC showed remaining starting material so additional dibenzyl N,N-dimethylphosphoramidite (0.300 mL, 1.13 mmol) was added and stirring continued for an additional 60 min. After cooling the mixture in an ice bath, THF (15 mL) was added, followed by dropwise addition of 30% $H_2O_2$ (3 mL). After stirring for 5 min., saturated aqueous $Na_2S_2O_3$ (60 mL) was added slowly. The mixture was diluted with water (100 mL) and extracted with $CH_2Cl_2$ (2×150 mL). The combined organic layers were dried ($Na_2SO_4$), filtered, and concentrated under reduced pressure. Purification by flash chromatography (40% ethyl acetate/hexanes) on silica gel followed by a second flash chromatography (50% ethyl acetate/hexanes) on silica gel furnished 182.9 mg product (63% yield) as a clear colorless oil.

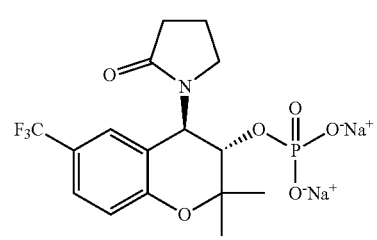

To a solution of dibenzyl ((3S,4R)-2,2-dimethyl-4-(2-oxopyrrolidin-1-yl)-6-(trifluoromethyl)chroman-3-yl) phosphate (92 mg, 0.156 mmol) in dry CH$_2$Cl$_2$ (10 mL) was added TMSBr (250 μL, 1.89 mmol) by syringe. After stirring for overnight, the reaction mixture was concentrated under reduced pressure. The resulting residue was purified by chromatography (0% acetonitrile/20 mM triethylammonium acetate buffer to 50% acetonitrile, C$_{18}$ column) to yield 71.5 mg white solid after lyophilization. To prepare the sodium salt of X, a 1 cm wide column was filled with 12 cm of DOWEX 50W2 (50-100 mesh, strongly acidic) ion exchange resin. The column was prepared by sequentially washing with 1:1 acetonitrile/water, 1M aqueous NaHCO$_3$ (lots of gas evolution), water, and then finally 1:1 acetonitrile/water. The reaction product was dissolved in 1:1 acetonitrile/water and loaded onto the column, which was eluted with 1:1 acetonitrile/water. The product containing fractions were lyophilized to furnish CKL-CF3 as a white solid (56.4 mg, 80% yield).

The present disclosure also provides aqueous-soluble compositions for the treatment of glaucoma and/or reducing intraocular pressure in patients. One of the composition is a Benzothiadiazine derivative which is soluble in aqueous solution. For example, the composition has the structure:

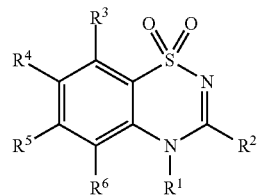

or

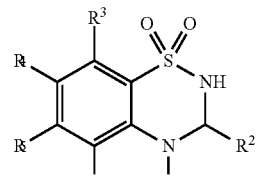

| R1 | R2 | R3 | R4 | R5 | R6 |
|---|---|---|---|---|---|
| 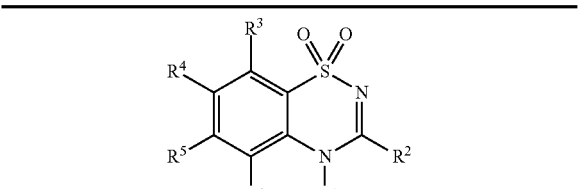 | —CH$_3$ | —H | —Cl | —H | —H |
| 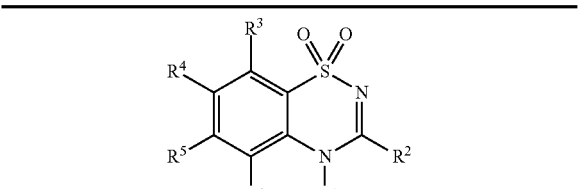 | —CH$_3$ | —H | —CF$_3$ | —H | —H |
| 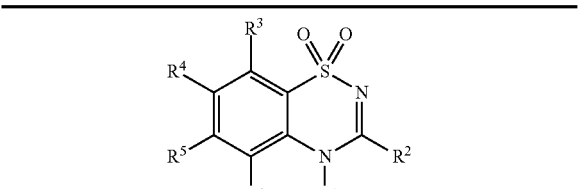 | —CH$_3$ | —H | —CH$_2$F$_3$ | —H | —H |
| 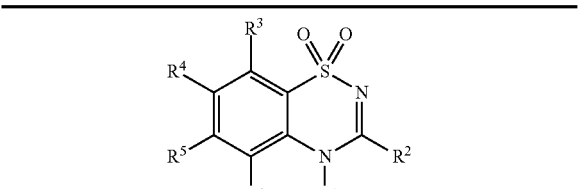 | —CH$_3$ | —H | —CH$_2$CF$_3$ | —H | —H |

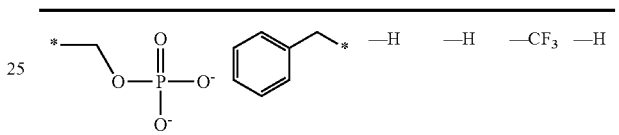

or

| R1 | R2 | R3 | R4 | R5 | R6 |
|---|---|---|---|---|---|
| 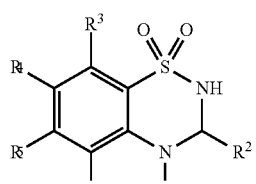 | 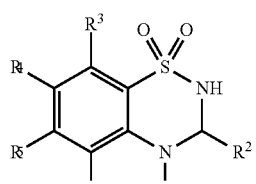 | —H | —H | —CF$_3$ | —H |
| 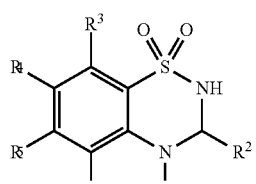 | | —H | —H | —SO$_2$NH$_2$ | —Cl | —H |
| 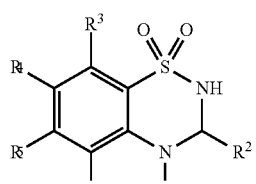 | | —H | —H | —SO$_2$NH$_2$ | —CF$_3$ | —H |
| —H | —CH$_2$N(CH$_3$)$_2$ | —H | —Cl | —H | —H |
| —H | —CH$_2$N(CH$_3$)$_2$ | —H | —CF$_3$ | —H | —H |
| —H | —CH$_2$N(CH$_3$)$_2$ | —H | —CH$_2$F$_3$ | —H | —H |
| —H | —CH$_2$N(CH$_3$)$_2$ | —H | —CH$_2$CF$_3$ | —H | —H |

It is understood that R1-R6 may individually be a functional group selected from Alkyl, Substituted alkyl, alkenyl, alkoxy, alkoxyalkyl, carbonylalkyl, alkoxyphosphonic acid, alkylcarbonylalkoxy, cycloalkyl, cycloalkenyl, heterocycle, sulfur group, halogen, hydrogen, nitrogen group, —CN, —CH$_2$F, —CF$_3$, —CF$_2$CF$_3$, —CF$_2$CF$_2$CF$_3$. Specific example, include:

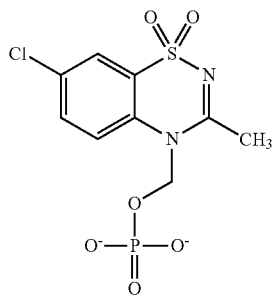

or

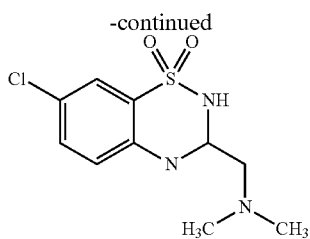

wherein R1 or R2 is a prodrug moiety of the formula:

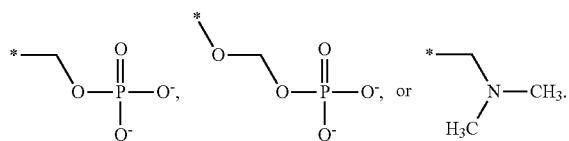

In addition, other protecting groups may be used

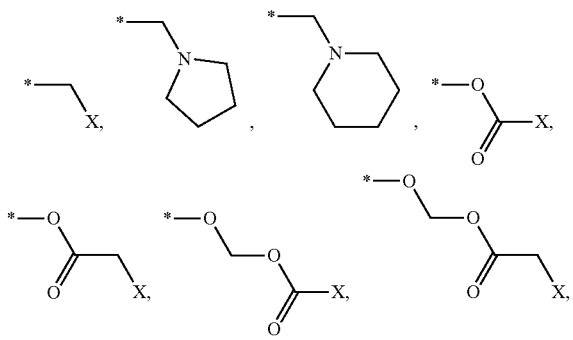

where X may be a Alkyl, Substituted alkyl, $C_3$-$C_8$ monocyclic cycloalkyl, $C_3$-$C_8$ monocyclic cycloalkenyl, 3- to 7-membered monocyclic heterocycle, 3- to 7-membered monocyclic heterocycle, e.g., azetidine, azete, oxetane, oxete, thietane, thiete, diazetidine, dioxetane, dioxete, pyrrolidine, pyrrole, tetrahydrofuran, furan, thiolane, thiophene, imidazolidine, imidazole, pyrazolidine, pyrazole, oxazolidine, oxazole, isoxazolidine, isoxazole, isothiazolidine, isothiazole, thiazolidine, thiazole, piperidine, or substituted variations thereof.

The present disclosure provides prodrug compositions of the parent compositions: 3-Benzyloxyamino-7-chloro-4H-1,2,4-benzothiadiazine 1,1-dioxide; 7-Chloro-3-methoxyamino-4H-1,2,4-benzothiadiazine 1,1-dioxide; 7-Bromo-3-isopropylamino-4H-1,2,4-benzothiadiazine 1,1-dioxide; 7-Chloro-3-(N-ethyl-N-methylamino)-4H-1,2,4-benzothiadiazine 1,1-dioxide; 6-Chloro-3-methoxyamino-4H-1,2,4-benzothiadiazine 1,1-dioxide; 6-Chloro-3-(1,2,2-trimethylpropyl)amino-4H-1,2,4-benzothiadiazine 1,1-dioxide; 7-Bromo-3-(1,2,2-trimethylpropyl)amino-4H-1,2,4-benzothiadiazine 1,1-dioxide; 6-Chloro-3-(N-ethyl-N-methylamino)-4H-1,2,4-benzothiadiazine 1,1-dioxide; 5-Amino-7-chloro-3-isopropylamino-4H-1,2,4-benzothiadiazine 1,1-dioxide; 7-Chloro-3-(1,3-dimethylpentyl)amino-4H-1,2,4-benzothiadiazine 1,1-dioxide; 7-Chloro-3-(1,5-dimethylhexyl)amino-4H-1,2,4-benzothiadiazine 1,1-dioxide; 7-Chloro-3-(1,4-dimethylpentyl)amino-4H-1,2,4-benzothiadiazine 1,1-dioxide; 5,7-Dichloro-3-isopropylamino-4H-1,2,4-benzothiadiazine 1,1-dioxide; 7-Bromo-6-trifluoromethyl-3-isopropylamino-4H-1,2,4-benzothiadiazine 1,1-dioxide; 7-Chloro-3-(3,3-diphenylpropylamino)-4H-1,2,4-benzothiadiazine 1,1-dioxide; 7-Chloro-3-(4-phenylbutylamino)-4H-1,2,4-benzothiadiazine 1,1-dioxide; 7-Chloro-3-(3-diethylamino-1-methylpropylamino)-4H-1,2,4-benzothiadiazine 1,1-dioxide; 3-Isopropylamino-4H-1,2,4-benzothiadiazine-5-carboxaldehyde 1,1-dioxide; 3-Isopropylamino-4H-1,2,4-benzothiadiazine-7-carboxaldehyde 1,1-dioxide; 3-Isopropylamino-4H-1,2,4-benzothiadiazine-6-carboxylic acid 1,1-dioxide; 7-Cyano-3-isopropylamino-4H-1,2,4-benzothiadiazine 1,1-dioxide; 6-Chloro-7-iodo-3-isopropylamino-4H-1,2,4-benzothiadiazine 1,1-dioxide; 6-Chloro-3-cyanomethylamino-4H-1,2,4-benzothiadiazine 1,1-dioxide; 5,7-Dichloro-3-isopropylamino-6-trifluoromethyl-4H-1,2,4-benzothiadiazine 1,1-dioxide; 7-Chloro-3-(3-(1H-imidazol-4-yl)propyl)amino-4H-1,2,4-benzothiadiazine 1,1-dioxide; 3-Isopropylamino-6,7-dimethoxy-4H-1,2,4-benzothiadiazine 1,1-dioxide; 3-(1-Azabicyclo[2.2.2]oct-3-yl)amino-7-chloro-4H-1,2,4-benzothiadiazine 1,1-dioxide; 6-Chloro-3-(1,2-dimethylpropyl)amino-4H-1,2,4-benzothiadiazine 1,1-dioxide; 6-Chloro-3-(1,2-dimethylpropyl)amino-7-sulfamoyl-4H-1,2,4-benzothiadiazine 1,1-dioxide; 3-Anilino-7-chloro-4H-1,2,4-benzothiadiazine 1,1-dioxide; 7-Chloro-3-(imidazol-2-yl)amino-4H-1,2,4-benzothiadiazine 1,1-dioxide; 7-Chloro-3-(4-pyridyl)amino-4H-1,2,4-benzothiadiazine 1,1-dioxide; 6-Chloro-3-isobutylamino-4H-1,2,4-benzothiadiazine 1,1-dioxide; 3-sec-Butylamino-6-chloro-4H-1,2,4-benzothiadiazine 1,1-dioxide; 6-Chloro-3-cyclohexylmethylamino-4H-1,2,4-benzothiadiazine 1,1-dioxide; 6-Fluoro-3-isopropylamino-4H-1,2,4-benzothiadiazine 1,1-dioxide; 3-Cyclopentylamino-6-fluoro-4H-1,2,4-benzothiadiazine 1,1-dioxide; 7-Chloro-3-isopropylamino-5-nitro-4H-1,2,4-benzothiadiazine 1,1-dioxide; 3-tert-Butylamino-6-chloro-4H-1,2,4-benzothiadiazine 1,1-dioxide; 7-Iodo-3-isopropylamino-4H-1,2,4-benzothiadiazine 1,1-dioxide; 6-Chloro-7-fluoro-3-isopropylamino-4H-1,2,4-benzothiadiazine 1,1-dioxide; 3-Isopropylamino-6-trifluoromethyl-4H-1,2,4-benzothiadiazine 1,1-dioxide; 7-Chloro-3-cyclopropylmethylamino-4H-1,2,4-benzothiadiazine 1,1-dioxide; 3-Isopropylamino-7-methyl-4H-1,2,4-benzothiadiazine 1,1-dioxide; 5,7-Dibromo-3-isopropylamino-4H-1,2,4-benzothiadiazine 1,1-dioxide; 6-Acetyl-3-isopropylamino-4H-1,2,4-benzothiadiazine 1,1-dioxide; 3-Allylamino-6-chloro-4H-1,2,4-benzothiadiazine 1,1-dioxide; 6-Chloro-3-(1-ethylpropyl)amino-4H-1,2,4-benzothiadiazine 1,1-dioxide; 6-Chloro-3-butylamino-4H-1,2,4-benzothiadiazine 1,1-dioxide; 6-Chloro-3-hexylamino-4H-1,2,4-benzothiadiazine 1,1-dioxide; 6,7-Dichloro-3-(1,2-dimethylpropyl)amino-4H-1,2,4-benzothiadiazine 1,1-dioxide; 6,7-Dichloro-3-(1-methylbutyl)amino-4H-1,2,4-benzothiadiazine 1,1-dioxide; 7-Chloro-3-(1,2-dimethylpropyl)amino-2-methyl-2H-1,2,4-benzothiadiazine 1,1-dioxide; 6,8-Dichloro-3-isopropylamino-4H-1,2,4-benzothiadiazine 1,1-dioxide; 7-Chloro-3-isopropylamino-2-methyl-2H-1,2,4-benzothiadiazine 1,1-dioxide; 3-Isopropylamino-6-benzenesulfonyl-4H-1,2,4-benzothiadiazine 1,1-dioxide; 3-Isopropylamino-6-methanesulfonyl-4H-1,2,4-benzothiadiazine 1,1-dioxide; 5-Chloro-3-isopropylamino-4H-1,2,4-benzothiadiazine 1,1-dioxide; 3-Isopropylamino-6-methyl-4H-1,2,4-benzothiadiazine 1,1-dioxide; 6-Chloro-3-isopropylamino-7-methyl-4H-1,2,4-benzothiadiazine 1,1-dioxide; 6-Ethoxycarbonylmethyl-3-isopropylamino-4H-1,2,4-benzothiadiazine 1,1-dioxide; 6-Carboxymethyl-3-isopropylamino-4H-1,2,4-benzothiadiazine 1,1-dioxide; 8-Chloro-3-isopropylamino-4H-1,2,4-benzothiadiazine 1,1-dioxide; 6-Isopropyl-3-isopropylamino-4H-1,2,4-benzothiadiazine 1,1-dioxide; 7-tert-Butyl-3-isopropylamino-4H-1,2,4-benzothiadiazine 1,1-dioxide; 3-Isopropylamino-6-phenoxy-4H-1,2,4-benzothiadiazine 1,1-dioxide; 6-Hexyl-3-isopropylamino-4H-1,2,4-benzothiadiazine 1,1-dioxide; 6-Cyclohexyl-3-isopropylamino-4H-1,2,4-benzothiadiazine 1,1-dioxide; 6-(3-Cyclopropyl-1,2,4-oxadiazol-5-yl)methyl-3-isopropylamino-4H-1,2,4-benzothiadiazine 1,1-dioxide; 6-Cyanomethyl-3-isopropylamino-4H-1,2,4-benzothiadiazine 1,1-dioxide; 7-Chloro-3-(2-phenylethyl)amino-4H-1,2,4-benzothiadiazine 1,1-dioxide; 3-sec-Butylamino-7-iodo-4H-1,2,4-benzothiadiazine 1,1-dioxide; 7-Iodo-3-(1,2-dimethylpropyl)amino-4H-1,2,4-benzothiadiazine 1,1-dioxide; 7-Iodo-3-(1,2,2-trimethylpropyl)amino-4H-1,2,4-benzothiadiazine 1,1-dioxide; 7-Chloro-3-cyclohexylmethylamino-4H-1,2,4-benzothiadiazine 1,1-dioxide; (R)-7-Chloro-3-(1-cyclohexylethyl)amino-4H-1,2,4-benzothiadiazine 1,1-dioxide; (S)-7-Chloro-3-(1-cyclohexylethyl)amino-4H-1,2,4-benzothiadiazine 1,1-dioxide; (R)-7-Chloro-3-(1-phenylethyl)amino-4H-1,2,4-benzothiadiazine 1,1-dioxide; (S)-7-Chloro-3-(1-phenylethyl)amino-4H-1,2,4-benzothiadiazine 1,1-dioxide; 3-Cyclohexyimethylamino-7-iodo-4H-1,2,4-benzothiadiazine 1,1-dioxide; (R)-3-(1-Cyclohexylethyl)amino-7-iodo-4H-1,2,4-benzothiadiazine 1,1-dioxide; (S)-3-(1-Cyclohexylethyl)amino-7-iodo-4H-1,2,4-benzothiadiazine 1,1-dioxide; 3-Benzylamino-7-iodo-4H-1,2,4-benzothiadiazine 1,1-dioxide; (R)-7-Iodo-3-(1-phenylethyl)amino-4H-1,2,4-benzothiadiazine 1,1-dioxide; (S)-7-Iodo-3-(1-phenylethyl)amino-4H-1,2,4-benzothiadiazine 1,1-dioxide; 3-sec-Butylamino-7-bromo-4H-1,2,4-benzothiadiazine 1,1-dioxide; 7-Bromo-3-(1,2-dimethylpropyl)amino-4H-1,2,4-benzothiadiazine 1,1-dioxide; 7-Fluoro-3-isopropylamino-4H-1,2,4-benzothiadiazine 1,1-dioxide; 3-sec-Butylamino-7-fluoro-4H-1,2,4-benzothiadiazine 1,1-dioxide; 7-Fluoro-3-(1,2-dimethylpropyl)amino-4H-1,2,4-benzothiadiazine 1,1-dioxide; 7-Bromo-3-cyclopropylamino-4H-1,2,4-benzothiadiazine 1,1-dioxide; 7-Chloro-3-cyclobutylamino-4H-1,2,4-benzothiadiazine 1,1-dioxide; 7-Chloro-3-(2,2,2-trifluoroethyl)amino-4H-1,2,4-benzothiadiazine 1,1-dioxide; 3-Isopropylamino-7-nitro-4H-1,2,4-benzothiadiazine 1,1-dioxide; 3-Allylamino-7-chloro-4H-1,2,4-benzothiadiazine 1,1-dioxide; 7-Chloro-3-(2-methoxy-1-methylethyl)amino-4H-1,2,4-benzothiadiazine 1,1-dioxide; 7-Chloro-3-(1-ethylpropyl)amino-4H-1,2,4-benzothiadiazine 1,1-dioxide; 3-(1-Ethylpropyl)amino-7-iodo-4H-1,2,4-benzothiadiazine 1,1-dioxide; 3-sec-Butylamino-7-nitro-4H-1,2,4-benzothiadiazine 1,1-dioxide; 3-(1,2-Dimethylpropyl)amino-7-nitro-4H-1,2,4-benzothiadiazine 1,1-dioxide; 7-Chloro-3-(2-hydroxypropyl)amino-4H-1,2,4-benzothiadiazine 1,1-dioxide; 7-Chloro-3-(2-hydroxy-1-methylethyl)amino-4H-1,2,4-benzothiadiazine 1,1-dioxide; 3-(2-Aminoethyl)amino-7-chloro-4H-1,2,4-benzothiadiazine 1,1-dioxide; 7-Chloro-3-(2,2-diethoxyethyl)amino-4H-1,2,4-benzothiadiazine 1,1-dioxide; 3-Ethylamino-7-fluoro-4H-1,2,4-benzothiadiazine 1,1-dioxide; 7-Fluoro-3-propylamino-4H-1,2,4-benzothiadiazine 1,1-dioxide; 3-Cyclopropylamino-7-fluoro-4H-1,2,4-benzothiadiazine 1,1-dioxide; 3-Cyclobutylamino-7-fluoro-4H-1,2,4-benzothiadiazine 1,1-dioxide; 3-Cyclopentylamino-7-fluoro-4H-1,2,4-benzothiadiazine 1,1-dioxide; 3-Cyclopropylmethylamino-7-fluoro-4H-1,2,4-benzothiadiazine 1,1-dioxide; 3-Allylamino-7-fluoro-4H-1,2,4-benzothiadiazine 1,1-dioxide; 7-Fluoro-3-(2-methoxy-1-methylethyl)amino-4H-1,2,4-benzothiadiazine 1,1-dioxide; 6-Chloro-3-cyclobutylamino-4H-1,2,4-benzothiadiazine 1,1-dioxide; 6-Chloro-3-(2,2,2-trifluoroethyl)amino-4H-1,2,4-benzothiadiazine 1,1-dioxide; 7-Bromo-3-methylamino-4H-1,2,4-benzothiadiazine 1,1-dioxide; 7-Bromo-3-ethylamino-4H-1,2,4-benzothiadiazine 1,1-dioxide; 7-Bromo-3-cyclobutylamino-4H-1,2,4-benzothiadiazine 1,1-dioxide; 7-Bromo-3-(2,2,2-trifluoroethyl)amino-4H-1,2,4-benzothiadiazine 1,1-dioxide; 7-Fluoro-3-methylamino-4H-1,2,4-benzothiadiazine 1,1-dioxide; 7-Chloro-3-hexylamino-4H-1,2,4-benzothiadiazine 1,1-dioxide; 6,7-Dichloro-3-hexylamino-4H-1,2,4-benzothiadiazine 1,1-dioxide; 3-(2,2-Diethoxyethyl)amino-7-fluoro-4H-1,2,4-benzothiadiazine 1,1-dioxide; 7-Fluoro-3-(2,2,2-trifluoroethyl)amino-4H-1,2,4-benzothiadiazine 1,1-dioxide; 7-Bromo-3-propylamino-4H-1,2,4-benzothiadiazine 1,1-dioxide; 6-Chloro-3-cyclopropylmethylamino-4H-1,2,4-benzothiadiazine 1,1-dioxide; 3-Cyclopropylmethylamino-7-nitro-4H-1,2,4-benzothiadiazine 1,1-dioxide; 7-Nitro-3-propylamino-4H-1,2,4-benzothiadiazine 1,1-dioxide; 3-Cyclobutylamino-7-nitro-4H-1,2,4-benzothiadiazine 1,1-dioxide; 6,7-Dichloro-3-cyclobutylamino-4H-1,2,4-benzothiadiazine 1,1-dioxide; 7-Amino-3-isopropylamino-4H-1,2,4-benzothiadiazine 1,1-dioxide; 7-Acetamido-3-isopropylamino-4H-1,2,4-benzothiadiazine 1,1-dioxide; 3-Cyclobutylamino-7-methyl-4H-1,2,4-benzothiadiazine 1,1-dioxide; 3-Isopropylamino-7-methoxy-4H-1,2,4-benzothiadiazine 1,1-dioxide; 7-Methoxy-3-propylamino-4H-1,2,4-benzothiadiazine 1,1-dioxide; 7-Chloro-3-(2-formylaminoethyl)amino-4H-1,2,4-benzothiadiazine 1,1-dioxide; 3-(2-Acetylaminoethyl)amino-7-chloro-4H-1,2,4-benzothiadiazine 1,1-dioxide; 5-Chloro-3-cyclobutylamino-4H-1,2,4-benzothiadiazine 1,1-dioxide; 5-Chloro-3-propylamino-4H-1,2,4-benzothiadiazine 1,1-dioxide; 5-Chloro-3-hexylamino-4H-1,2,4-benzothiadiazine 1,1-dioxide; 6-Chloro-3-octylamino-4H-1,2,4-benzothiadiazine 1,1-dioxide; 6-Chloro-3-(1,5-dimethylhexyl)amino-4H-1,2,4-benzothiadiazine 1,1-dioxide; 3-Isopropylamino-7-trifluoromethyl-4H-1,2,4-benzothiadiazine 1,1-dioxide; 3-sec-Butylamino-7-trifluoromethyl-4H-1,2,4-benzothiadiazine 1,1-dioxide; 3-Isopropylamino-4H-1,2,4-benzothiadiazine-7-carboxylic acid 1,1-dioxide; 3-sec-Butylamino-4H-1,2,4-benzothiadiazine-7-carboxylic acid 1,1-dioxide; 3-Propylamino-7-trifluoromethyl-4H-1,2,4-benzothiadiazine 1,1-dioxide; 3-Cyclopropylmethylamino-7-trifluoromethyl-4H-1,2,4-benzothiadiazine 1,1-dioxide; 3-Propylamino-4H-1,2,4-benzothiadiazine-7-carboxylic acid 1,1-dioxide; 7-Chloro-3-(pyridin-2-yl)amino-4H-1,2,4-benzothiadiazine 1,1-dioxide; 3-Ethylamino-6,7-difluoro-4H-1,2,4-benzothiadiazine 1,1-dioxide; 7-Fluoro-3,6-di(isopropylamino)-4H-1,2,4-benzothiadiazine 1,1-dioxide; 6,8-Difluoro-3-isopropylamino-4H-1,2,4-benzothiadiazine 1,1-dioxide; 6,7-Difluoro-3-isopropylamino-4H-1,2,4-benzothiadiazine 1,1-dioxide; 6,7,8-Trifluoro-3-isopropylamino-4H-1,2,4-benzothiadiazine 1,1-dioxide; 7-Fluoro-3-isopropylamino-6-methyl-4H-1,2,4-benzothiadiazine 1,1-dioxide; 7-Chloro-3-isopropylamino-6-methoxy-4H-1,2,4-benzothiadiazine 1,1-dioxide; 6,8-Dichloro-3-ethylamino-4H-1,2,4-benzothiadiazine 1,1-dioxide; 6,8-Dichloro-3-propylamino-4H-1,2,4-benzothiadiazine 1,1-dioxide; 6,8-Dichloro-3-cyclopropylamino-4H-1,2,4-benzothiadiazine 1,1-dioxide; 6,8-Dichloro-3-cyclopropylmethylamino-4H-1,2,4-benzothiadiazine 1,1-dioxide; 6,8-Dichloro-3-cyclobutylamino-4H-1,2,4-benzothiadiazine 1,1-dioxide; 6,8-Dichloro-3-cyclopentylamino-4H-1,2,4-benzothiadiazine 1,1-dioxide; 7-Chloro-3-(2-pyridyl)methylamino-4H-1,2,4-benzothiadiazine 1,1-dioxide; 7-Chloro-3-(3-pyridyl)methylamino-4H-1,2,4-benzothiadiazine 1,1-dioxide; 7-Chloro-3-(4-pyridyl)methylamino-4H-1,2,4-benzothiadiazine 1,1-dioxide; 7-Chloro-3-(2-pyridyl)ethylamino-4H-1,2,4- benzothiadiazine 1,1-dioxide; 7-Chloro-3-(3-pyridyl)ethylamino-4H-1,2,4-benzothiadiazine 1,1-dioxide; 7-Chloro-3-(4-pyridyl)ethylamino-4H-1,2,4-benzothiadiazine 1,1-dioxide; 6-Chloro-3-(2-pyridyl)methylamino-4H-1,2,4-benzothiadiazine 1,1-dioxide; 6-Chloro-3-(3-pyridyl)methylamino-4H-1,2,4-benzothiadiazine 1,1-dioxide; 6-Chloro-3-(4-pyridyl)methylamino-4H-1,2,4-benzothiadiazine 1,1-dioxide; 6-Chloro-3-(2-pyridyl)ethylamino-4H-1,2,4-benzothiadiazine 1,1-dioxide; 6-Chloro-3-(3-pyridyl)ethylamino-4H-1,2,4-benzothiadiazine 1,1-dioxide; 6-Chloro-3-(4-pyridyl)ethylamino-4H-1,2,4-benzothiadiazine 1,1-dioxide; 7-Fluoro-3-(2-pyridyl)methylamino-4H-1,2,4-benzothiadiazine 1,1-dioxide; 7-Fluoro-3-(3-pyridyl)methylamino-4H-1,2,4-benzothiadiazine 1,1-dioxide; 7-Fluoro-3-(4-pyridyl)methylamino-4H-1,2,4-benzothiadiazine 1,1-dioxide; 7-Fluoro-3-(2-pyridyl)ethylamino-4H-1,2,4-benzothiadiazine 1,1-dioxide; 7-Fluoro-3-(3-pyridyl)ethylamino-4H-1,2,4-benzothiadiazine 1,1-dioxide; 7-Fluoro-3-(4-pyridyl)ethylamino-4H-1,2,4-benzothiadiazine 1,1-dioxide; 6-Fluoro-3-(2-pyridyl)methylamino-4H-1,2,4-benzothiadiazine 1,1-dioxide; 6-Fluoro-3-(3-pyridyl)methylamino-4H-1,2,4-benzothiadiazine 1,1-dioxide; 6-Fluoro-3-(4-pyridyl)methylamino-4H-1,2,4-benzothiadiazine 1,1-dioxide; 6-Fluoro-3-(2-pyridyl)ethylamino-4H-1,2,4-benzothiadiazine 1,1-dioxide; 6-Fluoro-3-(3-pyridyl)ethylamino-4H-1,2,4-benzothiadiazine 1,1-dioxide; 6-Fluoro-3-(4-pyridyl)ethylamino-4H-1,2,4-benzothiadiazine 1,1-dioxide; 6,7-Dichloro-3-(2-pyridyl)methylamino-4H-1,2,4-benzothiadiazine 1,1-dioxide; 6,7-Dichloro-3-(3-pyridyl)methylamino-4H-1,2,4-benzothiadiazine 1,1-dioxide; 6,7-Dichloro-3-(4-pyridyl)methylamino-4H-1,2,4-benzothiadiazine 1,1-dioxide; 6,7-Dichloro-3-(2-pyridyl)ethylamino-4H-1,2,4-benzothiadiazine 1,1-dioxide; 6,7-Dichloro-3-(3-pyridyl)ethylamino-4H-1,2,4-benzothiadiazine 1,1-dioxide; 6,7-Dichloro-3-(4-pyridyl)ethylamino-4H-1,2,4-benzothiadiazine 1,1-dioxide; 6,8-Dichloro-3-(2-pyridyl)methylamino-4H-1,2,4-benzothiadiazine 1,1-dioxide; 6,8-Dichloro-3-(3-pyridyl)methylamino-4H-1,2,4-benzothiadiazine 1,1-dioxide; 6,8-Dichloro-3-(4-pyridyl)methylamino-4H-1,2,4-benzothiadiazine 1,1-dioxide; 6,8-Dichloro-3-(2-pyridyl)ethylamino-4H-1,2,4-benzothiadiazine 1,1-dioxide; 6,8-Dichloro-3-(3-pyridyl)ethylamino-4H-1,2,4-benzothiadiazine 1,1-dioxide; 6,8-Dichloro-3-(4-pyridyl)ethylamino-4H-1,2,4-benzothiadiazine 1,1-dioxide; 6,7-Difluoro-3-(2-pyridyl)methylamino-4H-1,2,4-benzothiadiazine 1,1-dioxide; 6,7-Difluoro-3-(3-pyridyl)methylamino-4H-1,2,4-benzothiadiazine 1,1-dioxide; 6,7-Difluoro-3-(4-pyridyl)methylamino-4H-1,2,4-benzothiadiazine 1,1-dioxide; 6,7-Difluoro-3-(2-pyridyl)ethylamino-4H-1,2,4-benzothiadiazine 1,1-dioxide; 6,7-Difluoro-3-(3-pyridyl)ethylamino-4H-1,2,4-benzothiadiazine 1,1-dioxide; 6,7-Difluoro-3-(4-pyridyl)ethylamino-4H-1,2,4-benzothiadiazine 1,1-dioxide; 6,8-Difluoro-3-(2-pyridyl)methylamino-4H-1,2,4-benzothiadiazine 1,1-dioxide; 6,8-Difluoro-3-(3-pyridyl)methylamino-4H-1,2,4-benzothiadiazine 1,1-dioxide; 6,8-Difluoro-3-(4-pyridyl)methylamino-4H-1,2,4-benzothiadiazine 1,1-dioxide; 6,8-Difluoro-3-(2-pyridyl)ethylamino-4H-1,2,4-benzothiadiazine 1,1-dioxide; 6,8-Difluoro-3-(3-pyridyl)ethylamino-4H-1,2,4-benzothiadiazine 1,1-dioxide; 6,8-Difluoro-3-(4-pyridyl)ethylamino-4H-1,2,4-benzothiadiazine 1,1-dioxide; 6,8-Bis(trifluoromethyl)-3-(1,4-dimethylpentyl)amino-4H-1,2,4-benzothiadiazine 1,1-dioxide; 6,8-Bis(trifluoromethyl)-3-isopropylamino-4H-1,2,4-benzothiadiazine 1,1-dioxide; 6,8-Bis(trifluoromethyl)-3-cyclopentylamino-4H-1,2,4-benzothiadiazine 1,1-dioxide; 6,8-Bis(trifluoromethyl)-3-cyclopropylamino-4H-1,2,4-benzothiadiazine 1,1-dioxide; 6,8-Bis(trifluoromethyl)-3-propylamino-4H-1,2,4-benzothiadiazine 1,1-dioxide; 6,8-Bis(trifluoromethyl)-3-cyclobutylamino-4H-1,2,4-benzothiadiazine 1,1-dioxide; 6.8-Bis(trifluoromethyl)-3-ethylamino-4H-1,2,4-benzothiadiazine 1,1-dioxide; 3-isopropylamino-4H-1,2,4-benzothiadiazine 1,1-dioxide; 3-isobutylamino-4H-1,2,4-benzothiadiazine 1,1-dioxide; (2-ethylhexylamino)-4H-1,2,4-benzothiadiazine 1,1-dioxide; cyclopropylamino-4H-1,2,4-benzothiadiazine 1,1-dioxide; cyclohexylamino-4H-1,2,4-benzothiadiazine 1,1-dioxide; 7-chloro-3-(1,2,2-trimethylpropylamino)-4H-1,2,4-benzothiadiazine 1,1-dioxide; 7-chloro-3-(1,2-dimethylpropylamino)-4H-1,2,4-benzothiadiazine 1,1-dioxide; 7-chloro-3-(1-methylpropylamino)-4H-1,2,4-benzothiadiazine 1,1-dioxide; 7-chloro-3-isopropylamino-4H-1,2,4-benzothiadiazine 1,1-dioxide; 7-chloro-3-cyclopropylamino-4H-1,2,4-benzothiadiazine 1,1-dioxide; 7-chloro-3-cyclohexylamino-4H-1,2,4-benzothiadiazine 1,1-dioxide; 6-chloro-3-isopropylamino-4H-1,2,4-benzothiadiazine 1,1-dioxide; 6-chloro-3-cyclopropylamino-4H-1,2,4-benzothiadiazine 1,1-dioxide; 6,7-dichloro-3-isopropylamino-4H-1,2,4-benzothiadiazine 1,1-dioxide; 6,7-dichloro-3-cyclopropylamino-4H-1,2,4-benzothiadiazine 1,1-dioxide; 3-isobutylamino-7-methyl-4H-1,2,4-benzothiadiazine 1,1-dioxide; 3-cyclopentylamino-7-methyl-4H-1,2,4-benzothiadiazine 1,1-dioxide; 3-cyclohexylamino-6-trifluoromethyl-4H-1,2,4-benzothiadiazine 1,1-dioxide; (N-cyclohexyl-N-methylamino)-4H-1,2,4-benzothiadiazine 1,1-dioxide; 3-cyclohexylamino-4-methyl-4H-1,2,4-benzothiadiazine 1,1-dioxide; 3-cyclohexylamino-2-methyl-2H-1,2,4-benzothiadiazine 1,1-dioxide.

The pharmaceutical composition of the present invention may be formulated into a variety of topically or injectable administrable ophthalmic compositions, such as solutions, suspensions, gels, ointments, micelles and emulsions such as water-in-oil emulsion or oil-in-water emulsion, the emulsion being cationic or anionic.

A liquid which is ophthalmically acceptable is formulated such that it can be administered topically to the eye. The comfort should be maximized as much as practicable, although sometimes formulation considerations (e.g. drug stability, bioavailability, etc.) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

Usually, said ophthalmic pharmaceutical composition is sterile. For ophthalmic application, solutions or medicaments are often prepared using a physiological saline solution as a major vehicle. Ophthalmic solutions are often maintained at a comfortable pH (usually within the range of pH 5.5-8) and an ophthalmically acceptable osmolality (generally about 150-450 mOsm, preferably 250-350 mOsm).

The formulations may also contain conventional, pharmaceutically acceptable preservatives, stabilizers and surfactants. Various buffers and means for adjusting pH may be used so long as the resulting preparation is ophthalmically acceptable. Accordingly, buffers include, but are not limited to, acetate buffers, citrate buffers, phosphate buffers, tris (hydroxymethyl)aminomethane (Tris) buffers and borate buffers. Acids or bases may be used to adjust the pH of these formulations as needed.

In another embodiment, the composition contains a preservative. Preservatives that may be used in the pharmaceutical compositions disclosed herein include, but are not limited to, cationic preservatives such as quaternary ammonium compounds including benzalkonium chloride, polyquad, and the like; guanidine-based preservatives including PHMB, chlorhexidine, and the like; chlorobutanol; mercury preservatives such as thimerosal, phenylmercuric acetate and phenylmercuric nitrate; and oxidizing preservatives such as stabilized oxychloro complexes.

In another embodiment, the composition contains a surfactant. A surfactant may be used for assisting in dissolving an excipient or an active agent, dispersing a solid or liquid in a composition, enhancing wetting, modifying drop size, or a number of other purposes. Useful surfactants include, but are not limited to surfactants of the following classes: alcohols; amine oxides; block polymers; carboxylated alcohol or alkylphenol ethoxylates; carboxylic acids/fatty acids; ethoxylated alcohols; ethoxylated alkylphenols; ethoxylated aryl phenols; ethoxylated fatty acids; ethoxylated; fatty esters or oils (animal and veg.); fatty esters; fatty acid methyl ester ethoxylates; glycerol esters; glycol esters; lanolin-based derivatives; lecithin and lecithin derivatives; lignin and lignin derivatives; methyl esters; monoglycerides and derivatives; polyethylene glycols; polymeric surfactants; propoxylated and ethoxylated fatty acids, alcohols, or alkyl phenols; protein-based surfactants; sarcosine derivatives; sorbitan derivatives; sucrose and glucose esters and derivatives.

In particular, ethoxylate surfactants are useful. An ethoxylate surfactants is one that comprises the moiety —O(CH$_2$CH$_2$O)$_n$—OH, wherein n is at least about 1.

Other excipient components which may be included in the ophthalmic preparations are chelating agents. A useful chelating agent is edetate disodium, although other chelating agents may also be used in place or in conjunction with it.

The present compositions in the form of aqueous suspensions may include excipients suitable for the manufacture of aqueous suspensions. Such excipients are suspending agents, for example, sodium carboxymethylcellulose, methylcellulose, hydroxypropyl-methylcellulose, sodium alginate, polyvinylpyrrolidone, gun tragacanth and gun acacia; dispersing or wetting agents may be a naturally occurring phosphatide, for example, lecithin, or condensation products of ethylene oxide with long chain aliphatic alcohols, for example, heptadeca-ethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example, polyoxyethylene sorbitan mono-oleate, and the like and mixtures thereof.

In one embodiment of the invention, said pharmaceutical composition as described here above is packaged in the form of unit dose. In one embodiment, said unit dose is a container capable of dispensing eye drops such as common manual bulb-operated pipette or small squeeze bottle with a dropper tip. In another embodiment, said unit dose is a container to which a device for the placement of eye drops may be applied. In another embodiment, said unit dose is a container capable of atomizing drops or droplets. In another embodiment, said unit dose is a disposable syringe.

In another embodiment, said pharmaceutical composition as described here above is for treating glaucoma. In one embodiment, glaucoma is selected in the group of primary open angle glaucoma (POAG), primary angle closure glaucoma, normal tension glaucoma (NTG), pediatric glaucoma, pseudoexfoliative glaucoma, pigmentary glaucoma, traumatic glaucoma, neovascular glaucoma, irido corneal endothelial glaucoma. Primary open angle glaucoma is also known as chronic open angle glaucoma, chronic simple glaucoma, glaucoma simplex.

In another embodiment, said pharmaceutical composition as described here above is for treating retinopathy, especially diabetic retinopathy and retinopathy of prematurity. In another embodiment, the pharmaceutical composition as described here above is for treating age related macular degeneration. In another embodiment, the pharmaceutical composition as described here above is for treating ocular hypertension including ocular hypertension resulting from trauma or surgery.

It will also be possible to incorporate the aqueous-soluble compositions of the present invention into controlled-release formulations and articles, where the total amount of compound is released over time, e.g., over a number of minutes or hours. The term controlled-release is used to define a release profile to effect delivery of an active over an extended period of time, defined herein as being between about 60 minutes and about 2, 4, 6 or even 8 hours. Controlled-release may also be defined functionally as the release of over 80 to 90 percent (%) of the active ingredient after about 60 minutes and about 2, 4, 6 or even 8 hours. Controlled-release as used herein may also be defined as making the active ingredient available to the patient or subject regardless of uptake. Typically, the total dosage of the compound will be within the limits described above for non-controlled-release formulations, but in some cases may be greater, particularly when the controlled release formulations act over relatively longer periods of time. Suitable controlled release articles for use with the compositions of the present invention include solid ocular inserts. Other controlled-release formulations may be based on polymeric carriers, including both aqueous-soluble polymers and porous polymers having desirable controlled-release characteristics, e.g., various cellulose derivatives, such as methylcellulose, sodium carboxymethylcellulose, hydroxyethylcellulose, and the like. Suitable porous polymeric carriers can be formed as polymers and copolymers of acrylic acid, polyacrylic acids, ethylacrylates, methylmethacrylates, polyacrylamides, and the like. Certain natural biopolymers may also find use, such as gelatins, alginates, pectins, agars, starches, and the like. A wide variety of controlled-release carriers are known in the art and available for use with the present invention. Topical compositions for delivering the aqueous-soluble compositions of the present invention will typically comprise the compound present in a suitable ophthalmically acceptable carrier, including both organic and inorganic carriers. Exemplary ophthalmically acceptable carriers include water, buffered aqueous solutions, isotonic mixtures of water and water-immiscible solvents, such as alkanols, arylalkanols, vegetable oils, polyalkalene glycols, petroleum-based jellies, ethyl cellulose, ethyl oleate, carboxymethylcelluloses, polyvinylpyrrolidones, isopropyl myristates, and the like. Suitable buffers include sodium chloride, sodium borate, sodium acetate, gluconates, phosphates, and the like. The formulations of the present invention may also contain ophthalmically acceptable auxiliary components, such as emulsifiers, preservatives, wetting agents, thixotropic agents (e.g., polyethylene glycols, antimicrobials, chelating agents, and the like). Particularly suitable antimicrobial agents include quaternary ammonium compounds, benzalkonium chloride, phenylmercuric salts, thimerosal, methyl paraben, propyl paraben, benzyl alcohol, phenylethanol, sorbitan, monolaurate, triethanolamine oleate, polyoxyethylene sorbitan monopalmitylate, dioctyl sodium sulfosuccinate, monothioglycerol, and the like. Ethylenediamine tetracetic acid (EDTA) is a suitable chelating agent. It will be understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. In addition, the present embodiments are meant to encompass both stereo chemical structures and combinations of different stereo chemical structures in the same composition. Such equivalents are considered to be within the scope of this invention and are covered by the claims.

What is claimed is:

1. A method to treat increased intraocular pressure, glaucoma, ocular hypertension, retinopathy, or age-related macular degeneration to a host in need thereof comprising administering an effective amount of a compound of the formula:

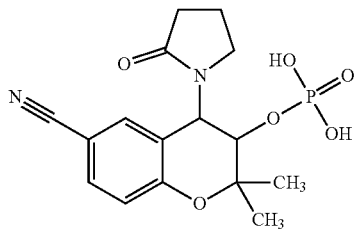 [SMILES: CC1(C)Oc2ccc(C#N)cc2C(N2CCCC2=O)C1OP(=O)(O)O]

optionally in a pharmaceutically acceptable carrier.

2. The method of claim 1, wherein the host is a human.
3. The method of claim 2 to treat increased intraocular pressure.
4. The method of claim 2 to treat ocular hypertension.
5. The method of claim 2 to treat glaucoma.
6. The method of claim 5, wherein the glaucoma is selected from primary open angle glaucoma, primary angle closure glaucoma, normal tension glaucoma, pediatric glaucoma, pseudoexfoliative glaucoma, pigmentary glaucoma, traumatic glaucoma, neovascular glaucoma, and irido corneal endothelial glaucoma.
7. The method of claim 6, wherein the glaucoma is primary open angle glaucoma.
8. The method of claim 6, wherein the glaucoma is pediatric glaucoma.
9. The method of claim 6, wherein the glaucoma is neovascular glaucoma.
10. The method of claim 6, wherein the glaucoma is normal tension glaucoma.
11. The method of claim 2 to treat retinopathy.
12. The method of claim 11, wherein the retinopathy is diabetic retinopathy.
13. The method of claim 2 to treat age related macular degeneration.
14. The method of claim 2, wherein the compound is of the formula:

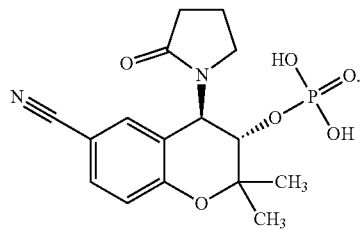 [SMILES: CC1(C)Oc2ccc(C#N)cc2[C@@H](N2CCCC2=O)[C@@H]1OP(=O)(O)O]

15. The method of claim 2, wherein the compound is of the formula:

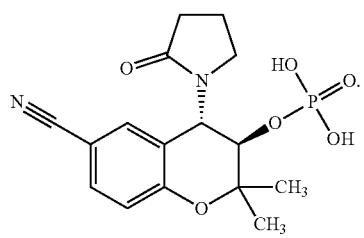 [SMILES: CC1(C)Oc2ccc(C#N)cc2[C@H](N2CCCC2=O)[C@H]1OP(=O)(O)O]

16. The method of claim 14 to treat increased intraocular pressure.
17. The method of claim 14 to treat ocular hypertension.
18. The method of claim 14 to treat glaucoma.
19. The method of claim 18, wherein the glaucoma is selected from primary open angle glaucoma, primary angle closure glaucoma, normal tension glaucoma, pediatric glaucoma, pseudoexfoliative glaucoma, pigmentary glaucoma, traumatic glaucoma, neovascular glaucoma, and irido corneal endothelial glaucoma.
20. The method of claim 19, wherein the glaucoma is primary open angle glaucoma.
21. The method of claim 19, wherein the glaucoma is pediatric glaucoma.
22. The method of claim 19, wherein the glaucoma is neovascular glaucoma.
23. The method of claim 19, wherein the glaucoma is normal tension glaucoma.
24. The method of claim 14 to treat retinopathy.
25. The method of claim 24, wherein the retinopathy is diabetic retinopathy.
26. The method of claim 14 to treat age related macular degeneration.
27. The method of claim 15 to treat increased intraocular pressure.
28. The method of claim 15 to treat ocular hypertension.
29. The method of claim 15 to treat glaucoma.
30. The method of claim 29, wherein the glaucoma is selected from primary open angle glaucoma, primary angle closure glaucoma, normal tension glaucoma, pediatric glaucoma, pseudoexfoliative glaucoma, pigmentary glaucoma, traumatic glaucoma, neovascular glaucoma, and irido corneal endothelial glaucoma.
31. The method of claim 30, wherein the glaucoma is primary open angle glaucoma.
32. The method of claim 30, wherein the glaucoma is pediatric glaucoma.
33. The method of claim 30, wherein the glaucoma is neovascular glaucoma.
34. The method of claim 30, wherein the glaucoma is normal tension glaucoma.

35. The method of claim 15 to treat retinopathy.

36. The method of claim 35, wherein the retinopathy is diabetic retinopathy.

37. The method of claim 15 to treat age related macular degeneration.

* * * * *